United States Patent [19]
Grevious

[11] Patent Number: 6,167,310
[45] Date of Patent: Dec. 26, 2000

[54] DOWNLINK TELEMETRY SYSTEM AND METHOD FOR IMPLANTABLE MEDICAL DEVICE

[75] Inventor: John J. Grevious, Minneapolis, Minn.

[73] Assignee: Medtronic, Inc., Minneapolis, Minn.

[21] Appl. No.: 09/283,028

[22] Filed: Mar. 31, 1999

[51] Int. Cl.[7] .................................................. A61N 1/362
[52] U.S. Cl. ............................................. 607/32; 607/60
[58] Field of Search ........................... 607/30–32, 59, 607/60; 128/903

[56] References Cited

U.S. PATENT DOCUMENTS

| | | |
|---|---|---|
| 4,211,235 | 7/1980 | Keller, Jr. . |
| 4,374,382 | 2/1983 | Markowitz . |
| 4,531,523 | 7/1985 | Anderson . |
| 4,539,992 | 9/1985 | Calfee et al. . |
| 4,550,732 | 11/1985 | Batty, Jr. et al. . |
| 4,556,063 | 12/1985 | Thompson et al. . |
| 4,571,589 | 2/1986 | Slocum et al. . |
| 4,676,248 | 6/1987 | Berntson . |
| 5,127,404 | 7/1992 | Wyborny et al. . |
| 5,292,343 | 3/1994 | Blanchette et al. . |
| 5,324,315 | 6/1994 | Grevious . |
| 5,350,411 | 9/1994 | Ryan et al. . |
| 5,476,488 | 12/1995 | Morgan et al. ........................... 607/30 |

*Primary Examiner*—George R. Evanisko
*Attorney, Agent, or Firm*—Thomas F. Woods; Harold R. Patton; Girma Wolde-Michael

[57] ABSTRACT

Downlink telemetry for an implantable medical device includes controlling downlink energy by generating a downlink strength signal representative of the strength of one or more downlink control bursts transmitted from an external communication device and received at the receiver of the implantable medical device. The peak amplitude of modulated downlink data bursts is controlled by adjusting the burst duration of the ramped envelope of such downlink data bursts as a function of the downlink strength signal.

46 Claims, 16 Drawing Sheets

DOWNLINK TELEMETRY SYSTEM AND METHOD FOR IMPLANTABLE MEDICAL DEVICE

FIELD OF THE INVENTION

The present invention relates to implantable medical devices. More particularly, the present invention pertains to implantable medical devices which include telemetry capabilities.

BACKGROUND OF THE INVENTION

As the complexity of implantable medical devices increases over time, telemetry systems for enabling such implantable medical devices to communicate with external communication devices, e.g., programmers, has become more important. For example, it is desirable for a physician to non-invasively exercise some amount of control over the implantable medical device, e.g., to turn the device on or off after implantation, to adjust various parameters of the implantable medical device after implantation, etc.

Further, as implantable medical devices include more advanced features, it is typically necessary to convey correspondingly more information to the implantable medical device relating to the selection and control of such advanced features. For example, if a pacemaker is selectively operable in various pacing modes, it is desirable that the physician be able to non-invasively select a mode of operation. Further, for example, if a pacemaker is capable of pacing at various rates, or of delivering stimulating pulses of varying energy levels, it is desirable that the physician be able to select, on a patient-by-patient basis, appropriate values for such variable operational parameters. Various types of information are conveyed to implanted medical devices by telemetry systems. For example, information conveyed to pacemakers may include, but is clearly not limited to, pacing modes, multiple rate response settings, electrode polarity, maximum and minimum pacing rates, output energy such as output pulse width and/or output current, sense amplifier sensitivity, refractory periods, calibration information, and rate response attack (acceleration) and decay (deceleration).

Not only has the complexity of implantable medical devices led to the need to convey correspondingly more information to the implantable medical device, but it has also become desirable to enable the implanted medical device to communicate information outside of the patient to an external communication device, e.g., programmer. For example, for diagnostic purposes it is desirable for the implanted device to be able to communicate information regarding its operational status to the physician. Various implantable medical devices are available which can transmit information to an external communication device, such as the transmission of a digitized ECG signal for display, storage, and/or analysis by the external communication device.

As used herein, the term "uplink" and "uplink telemetry" will be used to denote the communications channel for conveying information from the implanted medical device to an external communication device, e.g., a programmer. Conversely, the term "downlink" and "downlink telemetry" will be used to denote the communications channel for conveying information from an external communication device to the implanted medical device.

Various telemetry systems for providing the necessary communication channels between an external communication device and an implanted medical device have been described. For example, various telemetry systems are disclosed in the references listed in Table 1 below.

Typically, telemetry systems such as those described in Table 1 are employed in conjunction with an external programming/processing unit, e.g., an external communication device. A programmer for non-invasively programming a cardiac pacemaker is described in the following U.S. Patents to Hartlaub et al., each commonly assigned to the assignee of the present invention: U.S. Pat. No. 4,250,884, entitled "Apparatus For and Method Of Programming the Minimum Energy Threshold for Pacing Pulses to be Applied to a Patient's Heart;" U.S. Pat. No. 4,273,132, entitled "Digital Cardiac Pacemaker with Threshold Margin Check;" U.S. Pat. No. 4,273,133, entitled "Programmable Digital Cardiac Pacemaker with Means to Override Effects of Reed Switch Closure;" U.S. Pat. No. 4,233,985, entitled "Multi-Mode Programmable Digital Cardiac Pacemaker;" U.S. Pat. No. 4,253,466, entitled "Temporary and Permanent Programmable Digital Cardiac Pacemaker;" and U.S. Pat. No. 4,401,120, entitled "Digital Cardiac Pacemaker with Program Acceptance Indicator." Aspects of the programmer that are the subject of the foregoing Hartlaub et al. patents are also described in U.S. Pat. No. 4,208,008 to Smith, entitled "Pacing Generator Programming Apparatus Including Error Detection Means," and in U.S. Pat. No. 4,236,524 to Powell et al., entitled "Program Testing Apparatus."

Most commonly, telemetry systems for implantable medical devices employ a radio frequency (RF) transmitter and receiver in the implantable medical device, and a corresponding RF transmitter and receiver in the external communication device, e.g., programming unit. Within the implantable medical device, the transmitter and receiver use a an antenna for receiving downlink telemetry signals and for radiating RF signals for uplink telemetry. Specifically, the radiating RF signals are magnetically coupled through inductive (antenna) coils.

To communicate digital data using RF telemetry, a digital encoding scheme such as described in U.S. Pat. No. 5,127,404 to Wyborny et al., entitled "Improved Telemetry Format," is used. In particular, for downlink telemetry a pulse interval modulation scheme may be employed, wherein the external communication device, e.g., programmer, transmits a series of short RF "bursts" or pulses in which the duration of an interval between successive pulses, e.g., the interval from the trailing edge of one pulse to the trailing edge of the next pulse, encodes the data. For example, a shorter interval may encode a "0" bit while a longer interval may encode a "1" bit.

For uplink telemetry, pulse position modulation may be employed to encode uplink telemetry data. For pulse position modulation, a plurality of timeslots are defined in a data frame, and the presence or absence of pulses transmitted during each timeslot encodes the data. For example, a sixteen position data frame may be defined, wherein a pulse in one of the timeslots represents a unique four bit portion of data.

Programming devices typically interface with the implanted medical device through the use of a programming head or paddle. For example, generally, the programming head or paddle is a handheld unit adapted to be placed on or near the patient's body over the implant site of the patient's implanted medical device. The programming head may effect closure of a reed switch in the implantable medical device using a magnet to initiate a telemetry session. Thereafter, uplink and downlink communication may take place between the implanted medical device's transmitter/receiver and the receiver/transmitter of the external communication device. Other methods of initiating a telemetry session may also be used. For example, a wake-up pulse from an external communication device may be used to wake up the implanted medical device which polls its downlink receiver at an appropriate interval.

For programming arrangements, both uplink and downlink telemetry signal strength vary as a function of programming head positioning. Therefore, it is important for the programming head to be properly positioned over the patient's implant site so that downlink RF signals can be detected in the implantable medical device and uplink signals can be detected by the programming head. For example, if the programming head is too far away from the implantable medical device, the attenuation of RF signals transmitted across the boundary of the patient's skin may be too great, preventing the telemetry link from being established. Often, medical device programmers, for example, such as the Model 9710 or 9760 programmers commercially-available from Medtronic, Inc., are provided with a head positioning indicator, e.g., an audible or visible indicator, for indicating to a physician when the programming head is properly located over a patient's implanted medical device.

Conventionally, the technique used for determining when the programming head is properly positioned can be characterized as an "open loop" technique in that the determination of correct head positioning is based solely upon an assessment of whether the uplink signal (i.e., the signal transmitted from the implanted medical device to the external communication device) meets some minimum requirement. In such an open loop verification system, adequate downlink signal strength is not tested. For example, an open loop system for determining the proper positioning of a programming head is described in U.S. Pat. No. 4,531,523 to Anderson, entitled "Digital Gain Control for the Reception of Telemetry Signals from Implanted Medical Devices."

When downlink signal strength is not tested, it is important for the physician to be able to otherwise verify that programming RF signals transmitted from an external communication device are accurately received and processed by the implanted medical device. For example, circuitry in the implanted medical device may perform several different checks on the detected downlink telemetry signals, e.g., a parity check, and issue an acceptance signal if the downlink telemetry signals are found to be valid.

A communication protocol using handshaking can also be used to verify that a minimum downlink field strength for detection in the implanted medical device exists to signal a physician that correct head positioning has been achieved. However, conventional handshaking protocols do not provide any information useful for optimization of head positioning to ensure an adequate operating margin. In other words, proper programming head positioning may be indicated even though the programming head is actually marginally positioned, such that a very slight shift in positioning (e.g., due to patient motion) results in downlink telemetry failure.

One possible way to ensure an adequate margin between the strength of the downlink signals detected in an implanted medical device and the device's detection threshold (i.e., threshold below which detection does not occur) is to transmit downlink telemetry signals having much larger than nominal amplitudes. If extremely strong downlink signals are transmitted, the programmer could be assured that signals will be strong enough to exceed the detection threshold and be detected by the implanted medical device.

However, there are various disadvantages associated with excessively strong downlink telemetry signals. First, while power consumption is not a crucial factor in line-powered external communication devices, it is common for many programming devices to be portable and battery-powered so they are easily transported and can be used in a variety of clinical and/or non-clinical settings. For example, battery-powered programmers can be used by patients away from the clinical setting. It would be inefficient and undesirable to consume the limited battery power available for such devices with unnecessarily high energy downlink signals.

Perhaps a far greater disadvantage of transmitting high energy downlink signals is the possibility that the large RF energy bursts in the downlink transmission may interfere with the operation of the implanted medical device. Such interference may take various forms depending upon the implanted medical device. For example, magnetic field coupling into the lead system of a pacemaker during programming may occur. In other words, with use of high energy downlink telemetry bursts or pulses, it is possible for the downlink signals to induce voltages on implanted pace/sense leads. Such induced voltages may be interpreted by the implanted medical device's sensing circuitry as cardiac events and may thereby cause pacemaker inhibition. Further, such misinterpretation of cardiac events may lead to loss of synchronization with intrinsic cardiac activity.

Further, for example, excessively strong downlink telemetry signals have an electric field component that may cause misinterpreted signals to be provided to external communication devices. For example, various programmers provide ECG circuitry for detection of pacing pulses, and various ECG monitors are designed to process pacing artifacts. A strong downlink telemetry signal provides an electric field component that may be coupled onto a patient's skin during programming and handshake telemetry. Such coupling may undesirably present artifacts causing uncertainty when using skin electrodes to sense pacing pulses, e.g., false sensing of pacing pulses.

Furthermore, it is clinically possible for a patient to have more than one implanted device. If devices are implanted too close to one another, unintended communication to an adjacent device may become possible with excessive downlink energy.

U.S. Pat. No. 5,324,315 to Grevious, entitled "Closed-Loop Downlink Telemetry and Method for Implantable Medical Device," describes a closed-loop system in which one or more of the problems described above are addressed. In the system of U.S. Pat. No. 5,324,315, a specific type of downlink telemetry pulse is transmitted from the external communication device to the implanted medical device. In particular, the downlink pulses are RF bursts having a linear ramping envelope. The characteristics of the downlink burst envelope are such that the amplitude of the signal as detected by the implanted medical device's receiver, relative to the receiver's detection threshold, can be ascertained by measuring the time that the detected burst exceeds the receiver's detection threshold. This information can be communicated to the external communication device. In response to receipt of such information regarding the relative strength of the detected downlink signals, the external communication device can modulate the peak amplitude of the downlink burst envelopes by modulating the gain of the external communication device transmitter. As such, the external communication device can then ensure an adequate margin over the implanted medical device's detection threshold while at the same time avoiding the transmission of unnecessarily high energy downlink signals.

Table 1 below lists U.S. Patents relating to telemetry systems.

TABLE 1

| U.S. Pat. No. | Inventor(s) | Issue Date |
|---|---|---|
| 4,211,235 | Keller, Jr. | 8 July 1980 |
| 4,374,382 | Markowitz | 15 February 1983 |
| 4,531,523 | Anderson | 30 July 1985 |
| 4,539,992 | Calfee et al. | 10 September 1985 |
| 4,550,732 | Batty, Jr., et al. | 5 November 1985 |
| 4,556,063 | Thompson et al. | 3 December 1985 |
| 4,571,589 | Slocum et al. | 18 February 1986 |
| 4,676,248 | Berntson | 30 June 1987 |
| 5,127,404 | Wyborny et al. | 7 July 1992 |
| 5,292,343 | Blanchette et al. | 8 March 1994 |
| 5,324,315 | Grevious | 28 June 1994 |
| 5,350,411 | Ryan, et al. | 27 September 1994 |

All references listed in Table 1, and elsewhere herein, are incorporated by reference in their respective entireties. As those of ordinary skill in the art will appreciate readily upon reading the Summary of the Invention, Detailed Description of the Embodiments, and claims set forth below, at least some of the devices and methods disclosed in the references of Table 1 and elsewhere herein may be modified advantageously by using the teachings of the present invention. However, the listing of any such references in Table 1, or elsewhere herein, is by no means an indication that such references are prior art to the present invention.

SUMMARY OF THE INVENTION

The present invention has certain objects. That is, various embodiments of the present invention provide solutions to one or more problems existing in the prior art with respect to downlink telemetry. One of such problems involves the use of unnecessarily high energy downlink signals. Further, for example, other problems involve an undesirable amount of energy consumption, the potential for inducing voltages on implanted leads which may be misinterpreted by sensing circuitry of the implantable medical device, the coupling of electric field components of downlink telemetry onto a patient's skin resulting in the possible false sensing of pacing pulses, pacemaker inhibition due to induced voltages which may be misinterpreted by an implanted medical device's sensing circuitry, loss of synchronization with intrinsic cardiac activity due to magnetic field coupling into the lead system of an implantable medical device, unintended programming or communication, lack of adequate operating margins and maintenance of such margins during downlink telemetry, downlink telemetry failure, lack of ability to support easy measurement of downlink thresholds for implantable medical devices, and lack of ability to provide a self-adjusting technique to significantly reduce one or more of the above problems without sacrificing spatial performance or speed.

In comparison to known techniques for providing downlink telemetry, various embodiments of the present invention may provide one or more of the following advantages. For example, downlink magnetic field energy reduction is provided. As such, for example, inductive coupling of magnetic field energy into a lead system of an implanted medical device is reduced. Further, downlink energy reduction reduces the total energy consumption and shifts the energy spectrum upward away from sensitive regions of the spectrum, e.g., where other sensing functions are required.

In addition, downlink energy is adjusted by dynamically controlling burst width as required for adequate communication links, e.g., adequate coupling margin over the implanted medical device's detection threshold. Such margin is maintained while avoiding transmission of bursts of unnecessarily high energy. Further, an increase in downlink data rate may be provided by reducing maximum burst width, e.g., burst width below 150 $\mu$seconds. Such an increased downlink data rate shifts energy away from sensing circuitry of the implantable medical device. For example, an increased data rate from 1K baud to about 8K baud shifts energy away from an ECG sense amplifier band of a pacemaker.

Yet further advantages may include: the reduction of the likelihood of false pacing pulse detection by ECG circuitry in programmers because the peak-to-peak amplitude of electric field components is reduced in proportion to magnetic field intensity reduction; and due to the prevention of downlink overdriving, faster turn-around of implantable medical device transceivers is allowed so as to provide for a higher speed uplink protocol.

Some embodiments of the present invention include one or more of the following features: the provision of one or more downlink control bursts from a transmitter of an external communication device with each downlink control burst being defined by a ramped envelope having a burst duration and a peak amplitude; the detection of one or more downlink control bursts from a transmitter of an external communication device; the generation of a downlink strength signal representative of the strength of one or more downlink control bursts received at a receiver of an implantable medical device; the provision of a plurality of downlink data bursts from a transmitter of an external communication device, wherein each downlink data burst is defined by a ramped envelope having a burst duration and a peak amplitude and further wherein the peak amplitude of the downlink data bursts are controlled by adjusting the burst duration of the ramped envelope as a function of a downlink strength signal transmitted via uplink from an implantable medical device; the provision of a handshake between an external communication device and an implantable medical device, wherein the handshake is used to transmit one or more downlink control bursts from a transmitter of an external communication device to a receiver of the implantable medical device and is used for communicating a downlink strength signal generated by the implantable medical device back to the external communication device; the provision of a single downlink control burst by a transmitter of the external communication device, wherein a receiver of the implantable medical device is associated with circuitry for determining a time interval during which the single downlink control burst exceeds a detected signal threshold thereof, and further wherein the time interval is used for generating a downlink strength signal to be communicated back to the external communication device; adjustment of the burst duration of a ramped envelope of downlink data bursts to provide a threshold margin, e.g., at least 3 dB; provision of a certain number of downlink control bursts from a transmitter of an external communication device, wherein the burst duration and peak amplitude of each of the downlink control bursts is different; and detection of one or more downlink control bursts by counting the number of downlink control bursts received by a receiver of an implantable medical device and generating a downlink strength signal as a function of the counted number of downlink control bursts received thereby.

Still further, some embodiments of the present invention include one or more of the following features: an external communication device including a downlink transmitter operable to transmit one or more downlink control bursts and downlink data bursts with each of the bursts being defined by a ramped envelope having a burst duration and a peak amplitude; an implantable medical device having a downlink receiver operable to receive one or more downlink control bursts, detection circuitry to detect the strength of one or more downlink control bursts, and an uplink transmitter operable to transmit a downlink strength signal to an external communication device; a plurality of downlink data bursts from an external communication device whose peak amplitude is controlled by adjusting the burst duration of the ramped envelope thereof as a function of a downlink strength signal representative of the detected strength of one or more downlink control bursts detected by a receiver of an implantable medical device; an implantable medical device operable for carrying out a handshake with an external communication device, wherein the handshake is used to communicate one or more control bursts to the implantable medical device and further used to communicate a downlink strength signal to the external communication device; a downlink transmitter operable to transmit a single downlink control burst and timing circuitry associated with a downlink receiver to determine a time interval during which the single downlink control burst exceeds a detected signal threshold of the downlink receiver; a downlink transmitter operable to transmit a predetermined number of downlink control bursts, wherein each downlink control burst is defined by a ramped envelope having a burst duration and a peak amplitude and further wherein the burst duration and peak amplitude is different for each downlink control burst; and a counter associated with the downlink receiver for determining a number of downlink control bursts received by the downlink receiver of an implantable medical device, wherein a downlink strength signal is generated as a function of the counted number of downlink control bursts.

The above summary of the present invention is not intended to describe each embodiment of every implementation of the present invention. Advantages, together with a more complete understanding of the invention, will become apparent and appreciated by referring to the following detailed description and claims taken in conjunction with the accompanying drawings.

DETAILED DESCRIPTION OF THE EMBODIMENTS

Figure 1:
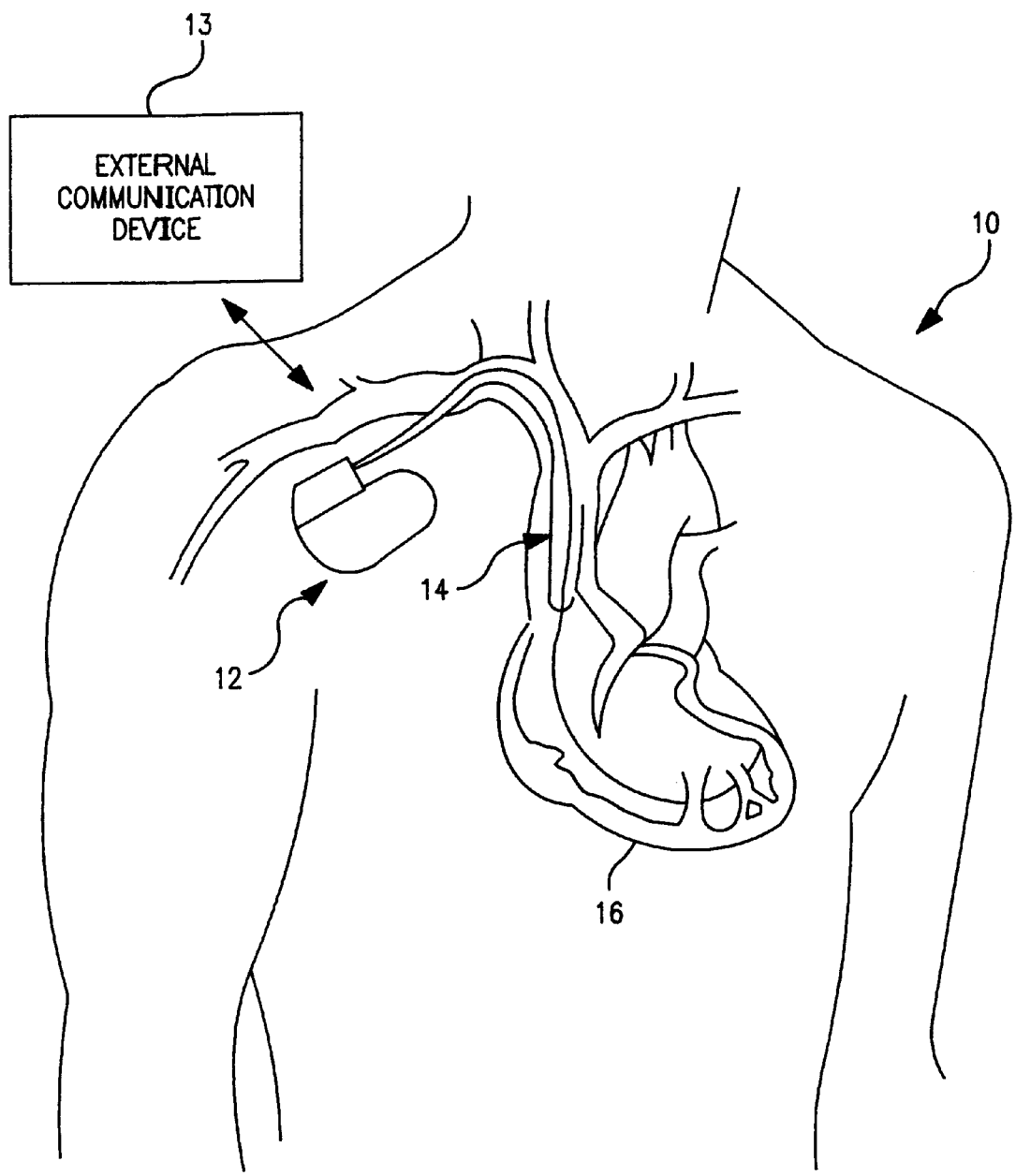
FIG. 1 is a diagram illustrating an implantable medical device in a body for communication with an external communication device, wherein the implantable medical device and external communication device provide downlink telemetry according to the present invention.

FIG. 1 is a simplified schematic view of an implantable medical device including telemetry circuitry for downlink communication with external communication device 13. According to the present invention, external communication device 13 provides one or more downlink control bursts. Each of the one or more downlink control bursts is defined by a ramped envelope having a burst duration and a peak amplitude. The implantable medical device 12 detects one or more of the downlink control bursts transmitted by the external communication device 13 and generates a downlink strength signal representative of the strength of one or more downlink control bursts received at the implantable medical device 12.

Further, the external communication device 13 provides downlink data bursts modulated with data. Such data bursts also are defined by a ramped envelope having a burst duration and a peak amplitude. The peak amplitude of the downlink data bursts transmitted by the external communication device 13 is controlled by adjusting the burst duration of the ramped envelope of the downlink data bursts as a function of the downlink strength signal representative of the strength of the one or more downlink control bursts received by the implantable medical device 12.

The link established for downlink telemetry between the external communication device 13 and implantable medical device 12 provides a closed-loop control for the downlink energy bursts transmitted by the external communication device 13. The downlink energy control leverages the ramp up and fast decay time of the RF bursts transmitted by the external communication device 13 for receipt by implantable medical device 12. By controlling the burst duration of the downlink data bursts from the external communication device 13, the peak amplitude and total energy for such bursts is reduced. For example, the burst on time for a transmitter of the external communication device 13 can be adjusted within a range of about 5 µseconds to about 150 µseconds.

Such downlink energy control shall be further described below with reference to FIGS. 5–8. Prior to describing such downlink energy control according to the present invention, various conventional downlink systems shall be described with reference to FIGS. 3–4.

As shown in FIG. 1, the implantable medical device 12 is implanted in a body 10 near a human heart 16. Implanted medical device 12 is electrically connected to the heart by leads 14. In the case where the implanted medical device 12 is a pacemaker, the leads 14 are pacing and sensing leads connected to the heart 16 from the implanted medical device 12. Such leads sense electrical signals attendant to the depolarization and repolarization of the heart 16 and provide pacing pulses for causing depolarization of cardiac tissue in the vicinity of the distal ends thereof. Implantable medical device 12 may be any implantable cardiac pacemaker such as those disclosed in U.S. Pat. No. 5,158,078 to Bennett et al.; U.S. Pat. No. 5,312,453 to Shelton et al.; or U.S. Pat. No. 5,144,949 to Olson.

Implantable medical device 12 may also be a pacemaker-cardioverter-defibrillator (PCD) corresponding to any of the various commercially-available implantable PCDs. For example, the present invention may be practiced in conjunction with PCDs such as those described in U.S. Pat. No. 5,545,186 to Olson et al.; U.S. Pat. No. 5,354,316 to Keimel; U.S. Pat. No. 5,314,430 to Bardy; U.S. Pat. No. 5,131,388 to Pless; or U.S. Pat. No. 4,821,723 to Baker, et al.

Alternatively, implantable medical device 12 may be an implantable nerve stimulator or muscle stimulator such as that disclosed in U.S. Pat. No. 5,199,428 to Obel et al.; U.S. Pat. No. 5,207,218 to Carpentier et al.; U.S. Pat. No. 5,330,507 to Schwartz; or an implantable monitoring device such as that disclosed in U.S. Pat. No. 5,331,966 issued to Bennett et al.

Further, for example, the implanted medical device 12 may be a defibrillator, a cardioverter-defibrillator, a brain stimulator, a gastric stimulator, a drug pump, a hemodynamic monitoring device, or any other implantable device that would benefit from a downlink telemetry system according to the present invention as described herein. Therefore, the present invention is believed to find wide application in any form of implantable medical device. As such, a description herein making reference to any particular medical device is not to be taken as a limitation of the type of medical device which can benefit from and which can employ a downlink telemetry system as described herein.

In general, the implantable medical device 12 may include a hermetically sealed enclosure that may include various elements such as an electrochemical cell (e.g., a lithium battery), circuitry that controls device operations and records rhythmic EGM episodes, telemetry transceiver antenna and circuitry that communicates with the external communication device 13 and provides a downlink telemetry system according to the present invention. Generally, the medical device is implemented with a microprocessor-based architecture. However, electronic features and operations of the implantable medical device may be implemented in discrete logic or as a microcomputer-based system, as would be readily apparent to one skilled in the art.

Figure 2:
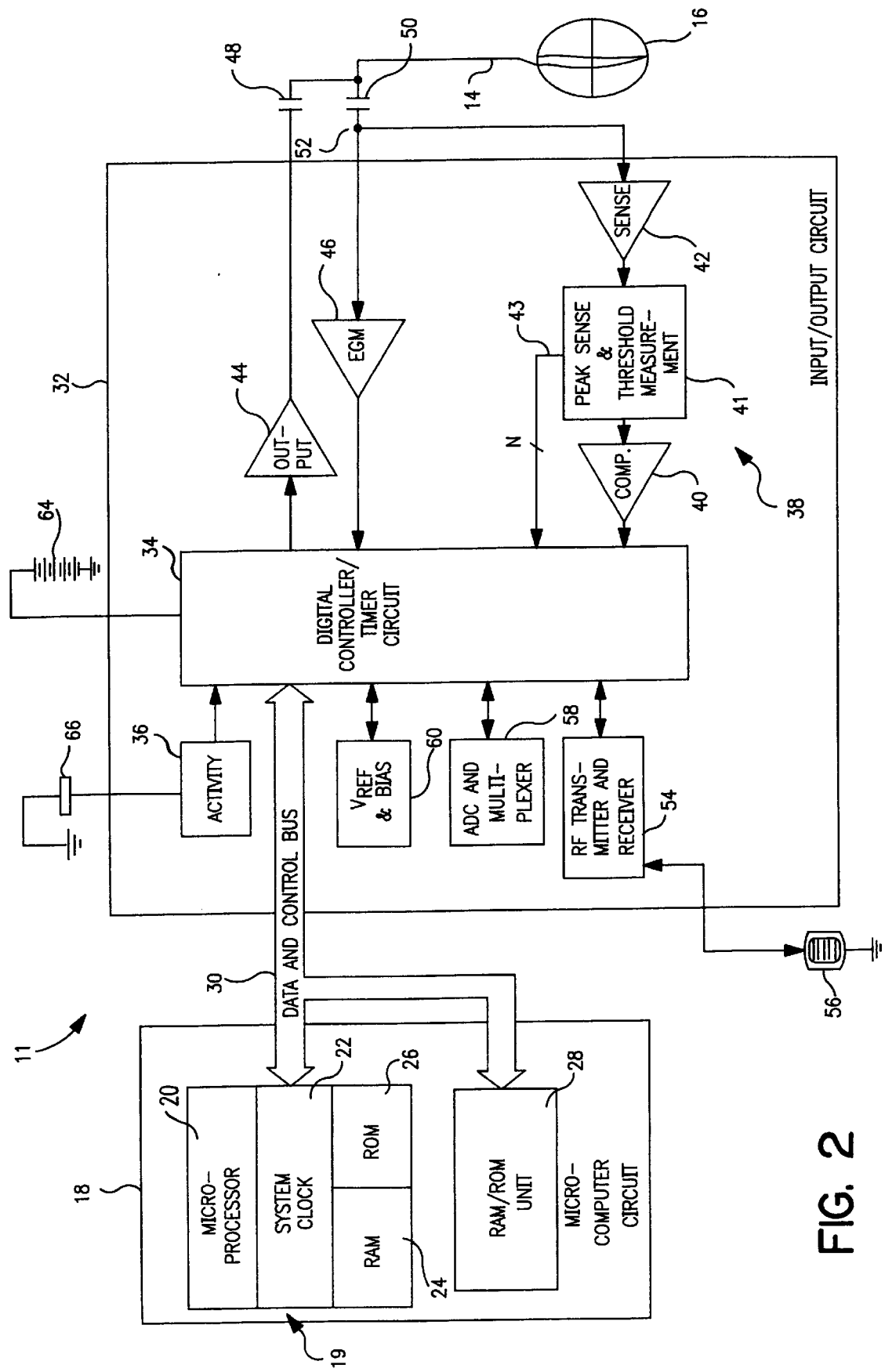
FIG. 2 is a general block diagram of circuitry of one embodiment of the implantable medical device of FIG. 1, including receiver and transmitter circuitry for use in downlink telemetry according to the present invention.

FIG. 2 shows a block diagram illustrating components of a pacemaker 11 in accordance with one embodiment of the present invention where pacemaker 11 has RF transmitter and receiver circuitry 54 for downlink telemetry according to the present invention. In the illustrative embodiment shown in FIG. 2, the pacemaker 11 is preferably programmable by means of an external programming unit, such as external communication device 13. One such programmer suitable for the purposes of the present invention is a commercially-available Medtronic Model 9710, 9765 or 9790 programmer. The programmer is a microprocessor based device which provides a series of encoded signals to pacemaker 11 by way of a programming head which transmits radiofrequency (RF) encoded burst signals to the telemetry subsystem components of pacemaker 11 according to the downlink telemetry system as described herein. Antenna 56 is connected to input/output circuit 32 to permit uplink/downlink telemetry through RF transmitter and receiver circuitry 54.

Pacemaker 11 illustratively shown in FIG. 2 is electrically coupled to the patient's heart 16 by lead 14. Lead 14 is coupled to a node 52 in the circuitry of pacemaker 11 through input capacitor 50. In the presently disclosed embodiment, an activity sensor 62 provides a sensor output to an activity circuit 36 of input/output circuit 32. Input/output circuit 32 also contains circuits for interfacing to heart 16, antenna 56, and contains circuits 44 for application of stimulating pulses to heart 16 to control its rate under control of software-implemented algorithms in microcomputer unit 18.

Microcomputer unit 18 preferably comprises on-board circuit 19 that includes microprocessor 20, system clock 22, and on-board random access memory (RAM) 24 and read-only memory (ROM) 26. In this illustrative embodiment, off-board circuit 28 comprises a RAM/ROM unit. On-board circuit 19 and off-board circuit 28 are each coupled by a communication bus 30 to digital controller/timer circuit 34.

The electrical components shown in FIG. 2 are powered by an appropriate implantable battery power source 64 in accordance with common practice in the art. For the sake of clarity, the coupling of battery power to the various components of pacemaker 11 is not shown in the figures.

$V_{REF}$ and bias circuit 60 generates a stable voltage reference and bias currents for circuits of input/output circuit 32. Analog to digital converter (ADC) and multiplexer unit 58 digitizes analog signals and voltages to provide "real-time" telemetry intracardiac signals and battery end-of-life (EOL) replacement function.

Operating commands for controlling the timing of pacemaker 11 are coupled by bus 30 to digital controller/timer circuit 34, where digital timers and counters establish the overall escape interval of the pacemaker as well as various refractory, blanking, and other timing windows for controlling the operation of the peripheral components disposed within input/output circuit 32. Digital controller/timer circuit 34 is preferably coupled to sense circuitry 38, including sense amplifier 42, peak sense and threshold measurement unit 41, and comparator/threshold detector 40. Sense amplifier 42 amplifies sensed electrocardiac signals and provides an amplified signal to peak sense and threshold measurement circuitry 41. Circuitry 41 in turn provides an indication of peak sensed voltages and measured sense amplifier threshold voltages on path 43 to digital controller/timer circuit 34. An amplified sense amplifier signal is also provided to comparator/threshold detector 40. Sense amplifier 42 may, for example, correspond to that disclosed in U.S. Pat. No. 4,379,459 to Stein.

Circuit 34 is further preferably coupled to electrogram (EGM) amplifier 46 for receiving amplified process signals sensed by an electrode disposed on lead 14. The electrogram signal provided by EGM amplifier 46 is employed when the implanted device is being interrogated by an external programmer, e.g., external communication device 13, to transmit by uplink telemetry a representation of an analog electrogram of the patient's electrical heart activity. Such functionality is, for example, shown in U.S. Pat. No. 4,556,063 to Thompson et al.

Output pulse generator 44 provides pulsing stimuli to the patient's heart 16 through coupling capacitor 48 in response to a pacing trigger signal provided by digital controller/timer circuit 34. Output amplifier 44, for example, may correspond generally to the output amplifier disclosed in U.S. Pat. No. 4,476,868 to Thompson.

Figure 3A:
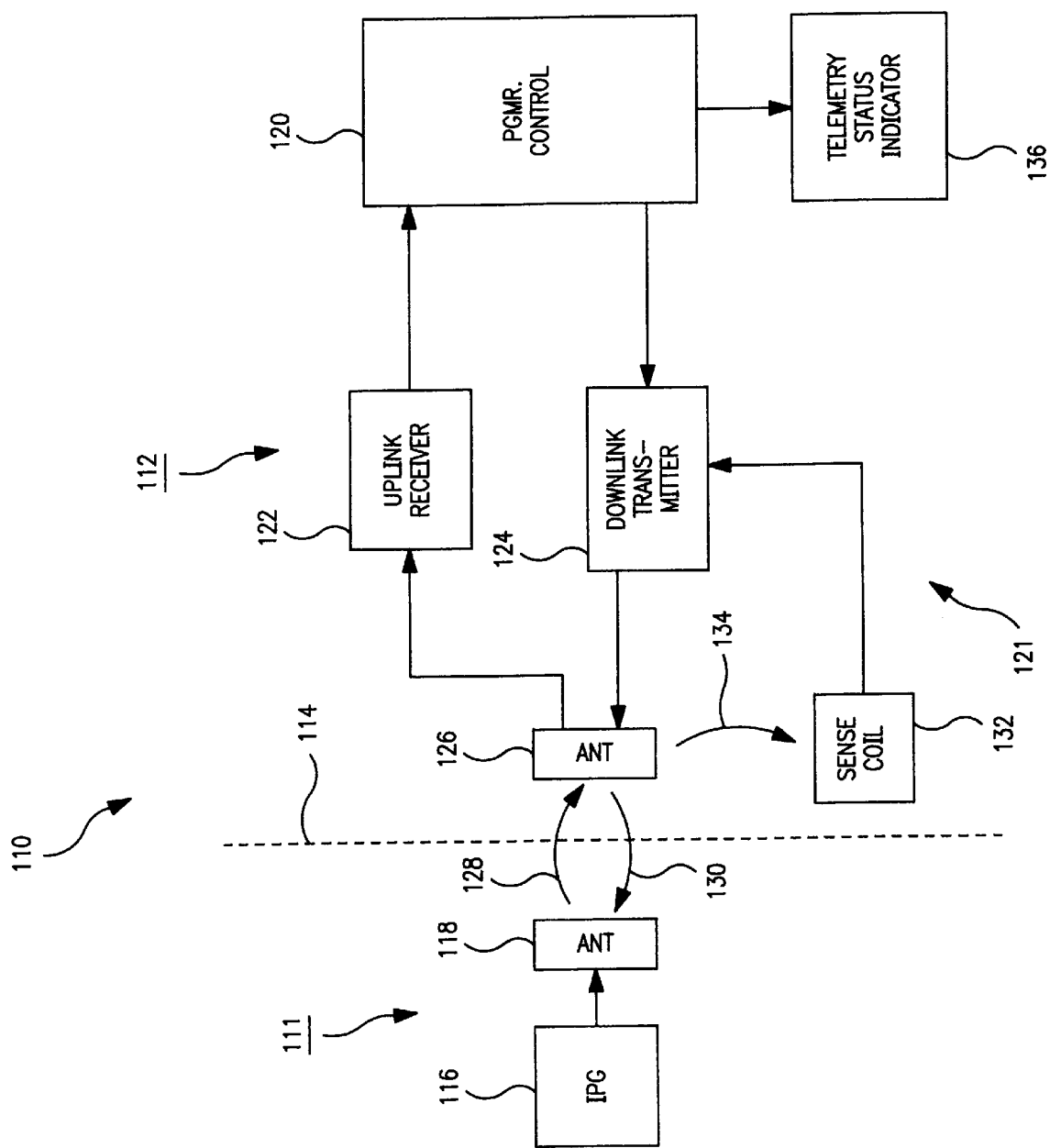
FIG. 3A is a block diagram of a prior art pacemaker and external communication device including an uplink/downlink telemetry system.

FIG. 3A is a block diagram of a prior art telemetry system 110 including an implantable medical device 111 and external communication device 112. A dashed line 114 in FIG. 3A represents the boundary (i.e., the patient's skin) between implanted medical device 111 and external communication device 112.

The implantable medical device 111 includes in this illustrative prior art embodiment an implantable pulse generator (IPG) system 116 in communication with an antenna 118. The antenna 118 may be of any antenna type utilized in implantable medical device applications for telemetry functions, e.g., "dual-coil" type antennas, multi-turn wire coil antennas, etc. The illustrative IPG system 116 includes a telemetry subsystem for receiving and storing downlink programming and control signals, and for providing various uplink signals to antenna 118 for transmission to external communication device 112.

Figure 3B:
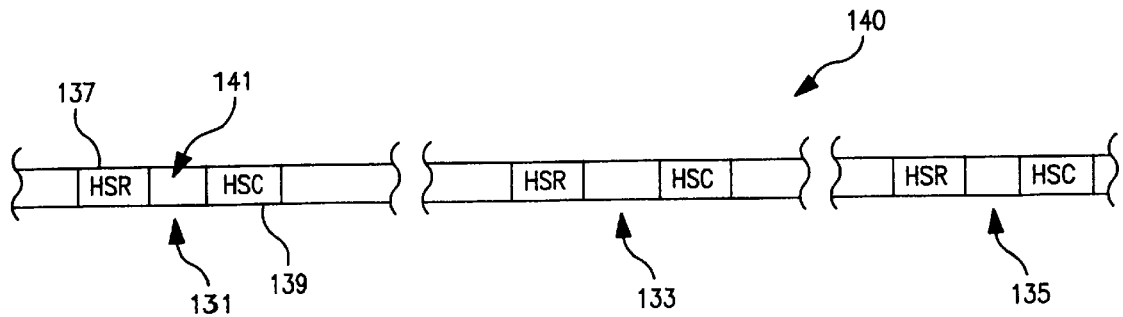
FIG. 3B is a diagram illustrating a handshake protocol for use in an uplink/downlink telemetry system such as that illustrated in FIG. 3A.
Figure 3C:
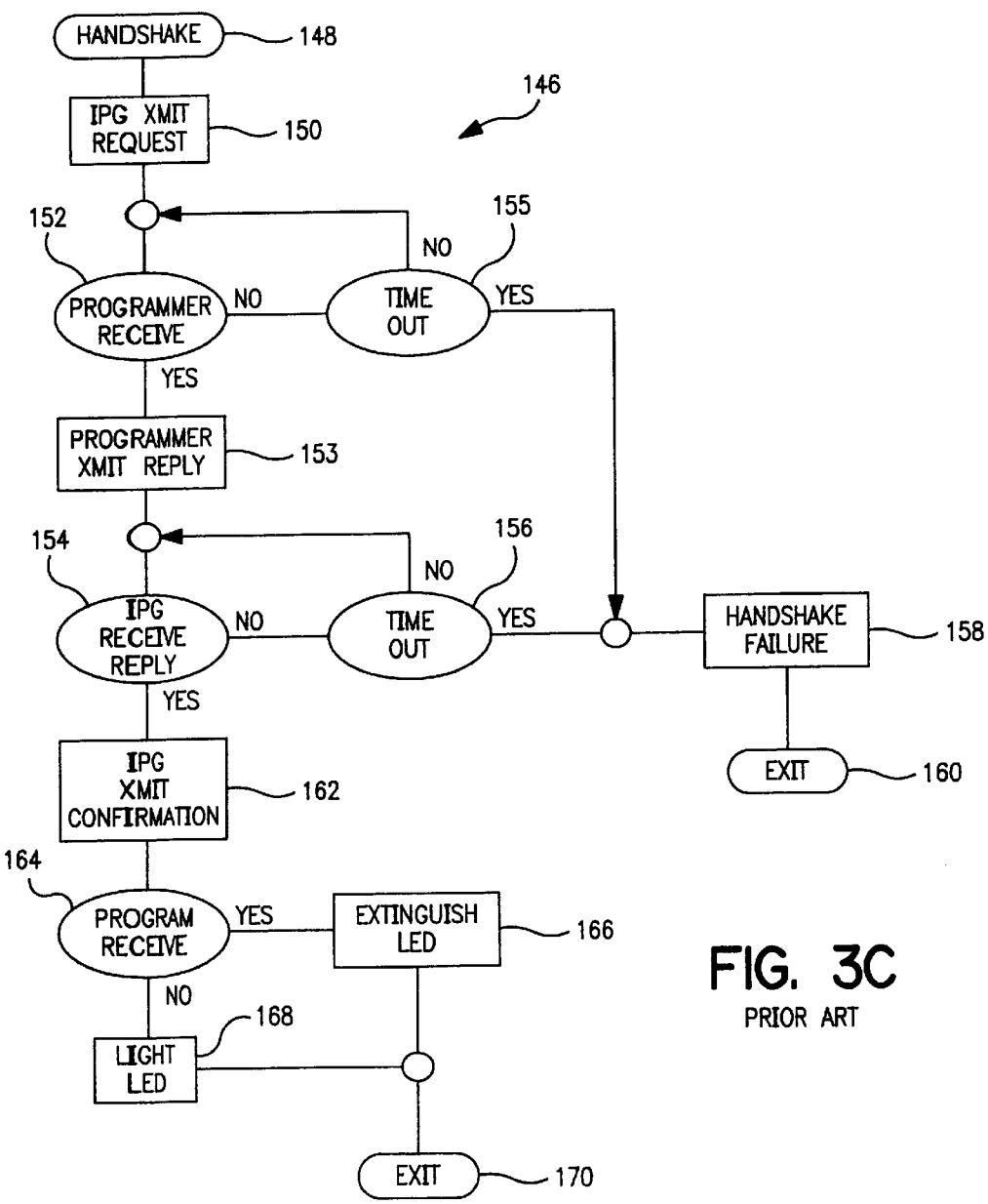
FIG. 3C is a flow diagram illustrating a handshake sequence of the handshake protocol of FIG. 3B.
Figure 3D:
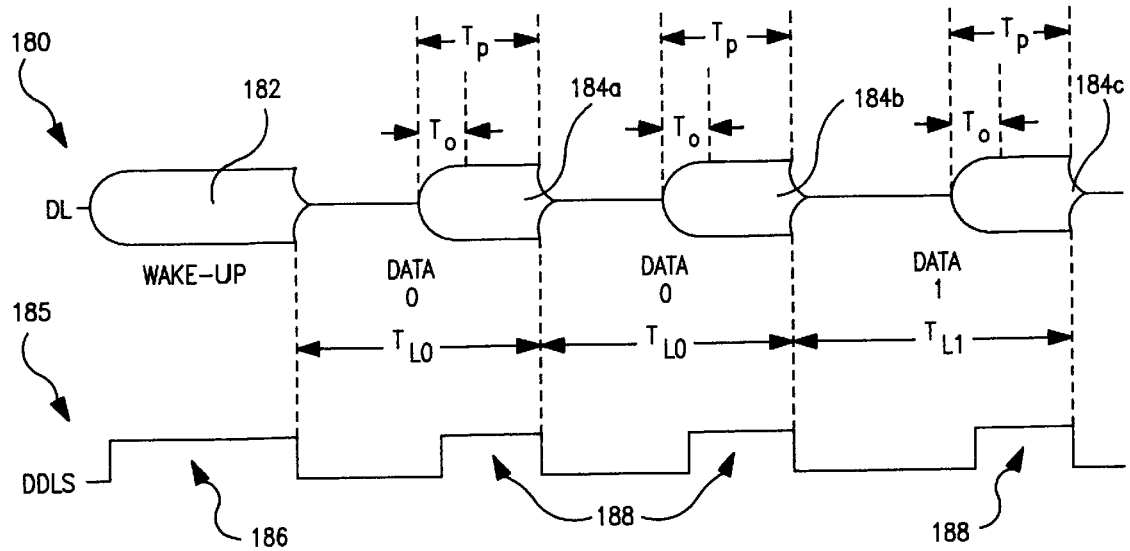
FIG. 3D is a diagram illustrating downlink burst envelopes for downlink telemetry and detection thereof for a prior art telemetry system such as that shown in FIG. 3A.
Figure 3E:
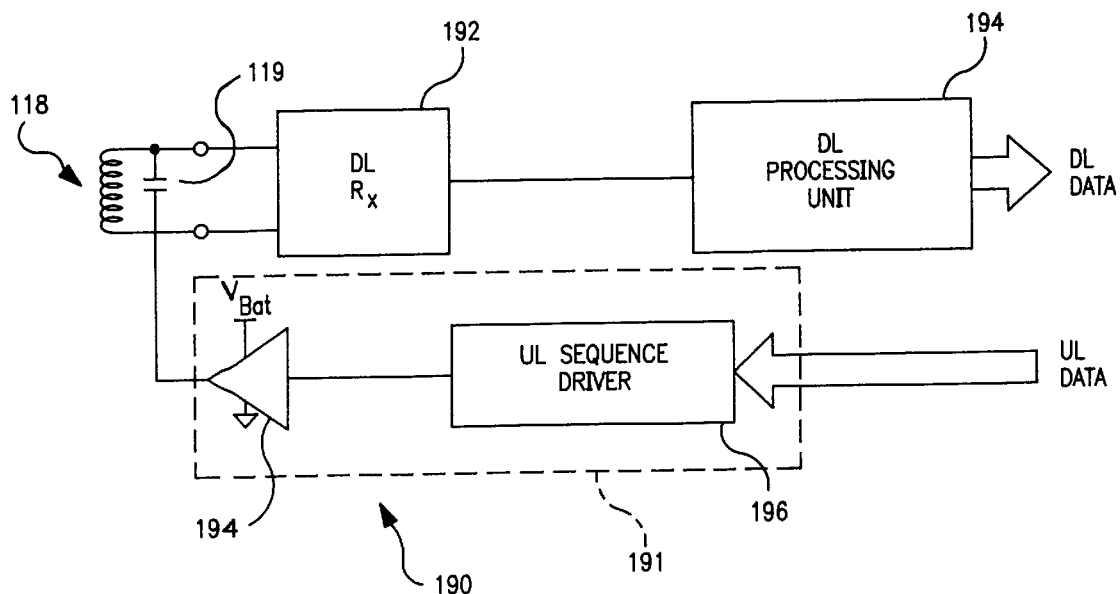
FIG. 3E is a block diagram illustrating one embodiment of prior art telemetry circuitry of an implantable medical device such as that shown in FIG. 3A for providing uplink/downlink telemetry.

FIG. 3E is a block diagram representative of one prior art embodiment of a telemetry subsystem 190 of the implantable medical device 111 of FIG. 3A which detects a burst stream 180 as transmitted by antenna 126 of the external communication device 112 and as generally shown by FIG. 3D. FIG. 3E shows a downlink processing unit 194 which receives demodulated information from downlink receiver 192. The downlink receiver output 185, as shown in FIG. 3D, represents the detected downlink signal of downlink receiver 192 representative of the bursts detected by the downlink receiver 192 received at antenna 118 and which exceed the detection threshold of the receiver. During downlink receive mode for the telemetry subsystem 190, the uplink transmitter circuitry 191 is AC grounded through capacitor 119. Uplink transmitter 191 receives uplink data at an uplink sequence driver 196 which provides an uplink sequence of information to uplink driver 194 for communication to external communication device 112 via antenna 118. Such a telemetry subsystem 190 is conventionally known and will not be described in further detail herein other than is necessary to describe the modification thereof necessary to provide for energy control of downlink bursts according to the present invention.

On the external side of the boundary 114, external communication device 112 is preferably implemented as a microprocessor-based system, such as in the case of Model 9710, 9765, or 9790 programming units manufactured and commercially-available from Medtronic, Inc. (Minneapolis, Minn.). External communication device 112 includes programmer control circuitry 120 coupled to subsystem telemetry circuitry 121. Such telemetry circuitry 121 includes an uplink telemetry receiver 122 and a downlink telemetry transmitter 124 coupled to an antenna 126. For example, as one skilled in the art will recognize, antenna 126 may be preferably disposed within a handheld programming head (not shown) so that the antenna may be conveniently placed above a patient's implant site. When so positioned, antenna 126 receives uplink telemetry signals transmitted from implanted medical device antenna 118, as indicated by arrow 128, and transmits downlink telemetry signals to be received by implanted medical device antenna 118, as indicated by arrow 130.

External communication device 112 may further preferably include a sense coil 132, also disposed in the programming head in proximity to antenna 126. Sense coil 132 is used to regulate the strength of downlink telemetry signals. In particular, sense coil 132 is adapted to receive the downlink telemetry signals transmitted from antenna 126 (as indicated by arrow 134) and to provide an indication of transmitted signal strength to transmitter 124. In other words, sense coil 132 functions as a type of automatic gain control (AGC). If the signal detected by sense coil 132 is too weak, the drive of transmitter 124 can be increased accordingly. Conversely, if sense coil 132 senses the downlink signal transmitted from antenna 126, and controlled by programmer control 120, is stronger than desired, the drive of transmitter 124 can be reduced.

Sense coil 132 is in a fixed relation with respect to antenna 126 and is therefore capable only of sensing the transmitted strength of the downlink signals. In other words, the strength of the signals actually detected by the implanted medical device's receiver 192 is not detected. Sense coil 132 is not capable of determining the strength of downlink signals as received by implanted medical device antenna 118 after such signals have been transmitted across implant boundary 114. Thus, even if downlink signals are determined by the sense coil 132 to be sufficiently strong, improper positioning of the programming head with respect to implanted antenna 118 may nonetheless prevent the downlink signals from being received by the implantable medical device 111.

To provide feedback as to the proper positioning of external antenna 126 with respect to implanted medical device antenna 118, prior art devices have employed a position indicator 136. For example, the position indicator 136 may be an audible tone generator and/or a visible indicator such as a light emitting diode (LED) or any other indicator. When uplink telemetry signals are received by antenna 126 and receiver 122, the strength of the received signals can be assessed and the accuracy of the uplink signal contents can be verified, as with parity checking, error checking codes, and the like, embedded in the uplink signal. When uplink signal strength and accuracy are confirmed, programmer control circuit 120 will cause position indicator 136 to indicate that an uplink telemetry link has been established. If adequate signal strength and content accuracy cannot be confirmed (i.e., if the uplink telemetry link is broken), position indicator 136 will so indicate such failure. As such, the physician is required to move the programming head around until uplink telemetry can be re-established. However, establishment of an uplink channel does not mean that proper positioning and downlink energy strength is sufficient for establishing a downlink channel, e.g., coupling for uplink and downlink may differ as is the case for dual coil antennas.

The establishment of a downlink channel between the implantable medical device 111 and external communication device 112 has conventionally been performed with use of a handshake protocol, such as handshake protocol 140 shown generally in FIG. 3B. For example, upon a successful handshake, telemetry status indicator 136 may indicate that a link is established. Generally, the handshake protocol 140 is performed in a manner such as that described in U.S. Pat. No. 5,292,343 to Blanchette et al., entitled "Handshake for Implanted Medical Device Telemetry." A periodically scheduled handshake sequence 131, 133, 135 is scheduled, e.g., about four times a second.

The handshake protocol may be initiated by any one of a number of techniques. For example, a telemetry session may be initiated thereby starting the handshake protocol by the closing of a reed switch of the implanted medical device 111 as is known in the art, may be initiated by a wake-up pulse, or by any other technique of beginning a telemetry session. After initiation of the telemetry session, a handshake sequence is periodically performed. Generally, the handshake sequence includes a handshake request 137, a window 141 for response to the request, and a handshake confirmation 139, as shown in FIG. 3B. One skilled in the art will recognize that either the implantable medical device 111 or the external communication device 112 may be used to initiate the handshake sequences with a handshake request. Preferably, according to the present invention, the handshake sequences are initiated by a handshake request 137 from the implantable medical device as further described below. The present invention which controls the energy of downlink bursts by controlling the burst duration uses the handshake sequence to communicate information from the implantable medical device to the external communication device to facilitate such energy control. As such, the control may be periodically updated with each handshake sequence.

FIG. 3C shows one illustrative embodiment of a prior art handshake procedure 146 which may be used for communication with the telemetry system 110 of FIG. 3A and which may be used according to the present invention in a modified form, as further described below. The handshake sequence 146 is initiated at handshake block 148. It will be recognized that each handshake sequence 131, 133, 135 and so on is periodically carried out during an initiated telemetry session. In the illustrative embodiment, the implantable medical device, e.g., an IPG, transmits the handshake request 137 at block 150. The transmitted handshake request is a frame having a unique frame identifier without any data pulses or data bursts.

If the external communication device 112, e.g., programmer, receives the handshake request 137 as determined at block 152, then external communication device 112, e.g., programmer, transmits a handshake reply (block 153) during the handshake reply window 141. If the programmer does not receive the handshake request 137, a timeout period (block 155) is issued so as to continue waiting for the handshake request 137. If during the timeout the external communication device 112 receives a handshake request 137, a handshake reply (block 153) is issued. Block 156 illustrates that some time during the timeout is expended by the implanted medical device 111 in waiting for the handshake reply. If during the timeout no handshake reply is received by the implanted medical device 111 indicating that the handshake request 137 was not received by external communication device 112, a handshake failure (block 158) is issued and the handshake sequence is exited (block 160) until the next periodic handshake sequence.

A properly timed reply during the reply window 141 from the external communication device 112 received by the implantable medical device 111 causes transmission of a handshake confirmation 139 (block 162). Upon receipt of the confirmation 139 by the external communication device 112 (block 164), an indication that a link is established is provided, e.g., an LED is extinguished (block 166). Likewise, an indication that the confirmation was not received may also be indicated in some manner, e.g., an LED is lighted (block 168). Thereafter, the handshake sequence is exited (block 170).

Therefore, generally, the handshake sequence 131, 133, 135 is initiated by the implantable medical device 111 and for this reason is called uplink and schematically consists of a handshake request 131 uplink from the implantable medical device 111, a handshake reply in window 141 downlink from the external communication device 112, and a final handshake confirmation 139 uplink from the implantable medical device 111. All three transmissions must be completed successfully for the handshake to be considered valid and for a link to be established. The handshake request 137 and handshake confirmation 139 are in the form of back-to-back frames transmitted by the implantable medical device 111.

The operation of the prior art telemetry system 110 of FIG. 3A is further described with reference to FIG. 3D. In FIG. 3D, there is depicted a portion of a downlink burst stream 180 employed in prior art telemetry. As previously noted herein, downlink telemetry has been known to be performed in the prior art using a pulse interval modulation scheme, wherein digital information (1's and 0's) is encoded into a pulse stream by modulating the trailing edge to trailing edge time between successive bursts. As shown in FIG. 3D, each burst 184a–c of burst stream 180 following an initial wake-up burst 182 lasts for a predetermined duration, $T_p$, and typically has a nonlinear increase in the envelope amplitude on the rising edge over a time period ($T_0$) and a rapid fall time at the trailing edge.

As shown in FIG. 3D, the bursts 184a–c are envelopes of radio frequency oscillating signal. Preferably, the downlink bursts 184a–c are bursts of a 175 kHertz oscillating signal. For example, in one embodiment, each burst lasts for $T_p$ of about 350 μseconds, and includes an initial rising portion lasting for $T_0$ of about 100 μseconds or less.

As shown in FIG. 3D, pulse interval modulation is used which involves varying the time between the trailing edges of two successive bursts in the downlink telemetry burst stream 180. The interval between the trailing edge of burst 184a and the trailing edge of burst 184b designated "$T_{L0}$" represents the time interval corresponding to a binary "0" encoded into the stream 180 while the interval between the trailing edge of burst 184b and burst 184c designated "$T_{L1}$" represents the time interval corresponding to a binary "1" encoded into the stream 180. One skilled in the art will recognize that various intervals may be used to encode the "0's" and "1's."

The detected downlink signal waveform 185 is representative of the downlink receiver output representative of the bursts in burst stream 180 detected by the downlink receiver 192 of the telemetry subsystem 190 of the implantable medical device 111. For example, square wave 186 corresponds to the wake-up burst 182 and the other square waves 188 represent the detected bursts 184a–c. The square waves 188 are of a lesser duration as described further below than the burst duration $T_p$ of bursts 184a–c as the downlink receiver 192 includes a detection threshold under which the bursts 184a–c are not detected. In other words, the downlink receiver 192 recognizes the bursts 184 only upon sufficient ramp up of the bursts 184a–c.

The bursts 184a–c are of a burst duration which is relatively large compared to the downlink bursts provided according to the present invention. As such, downlink bursts 184a–c consume a larger quantity of energy and further lead to the problems as describe in the background of the invention section herein. In particular, the present invention makes use only of rising edges of bursts similar to bursts 184a–c. Generally, such rising edges are less than 150 μseconds in duration and, preferably generally linear.

Figure 4A:
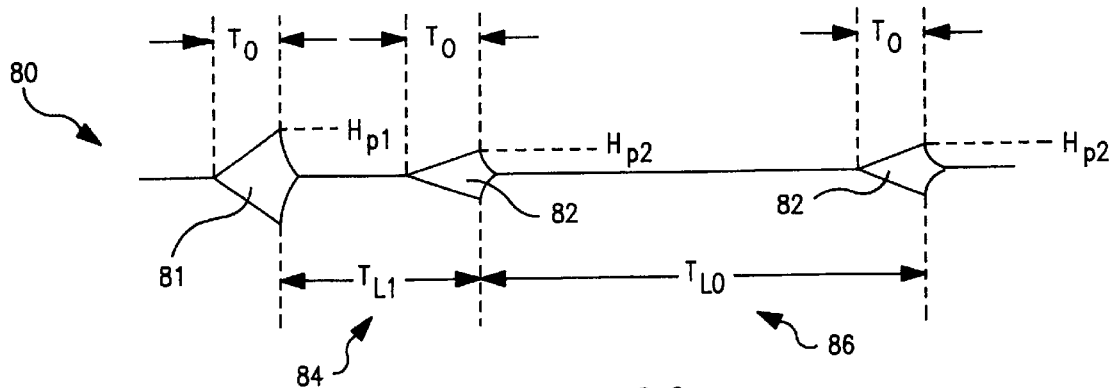
FIGS. 4A and 4B are diagrams illustrating a prior art closed-loop technique for modulating the peak amplitude of downlink burst envelopes based upon information provided from the implanted medical device regarding the relative strength of detected downlink signals from an external communication device as described in U.S. Pat. No. 5,324,315.
Figure 4B:
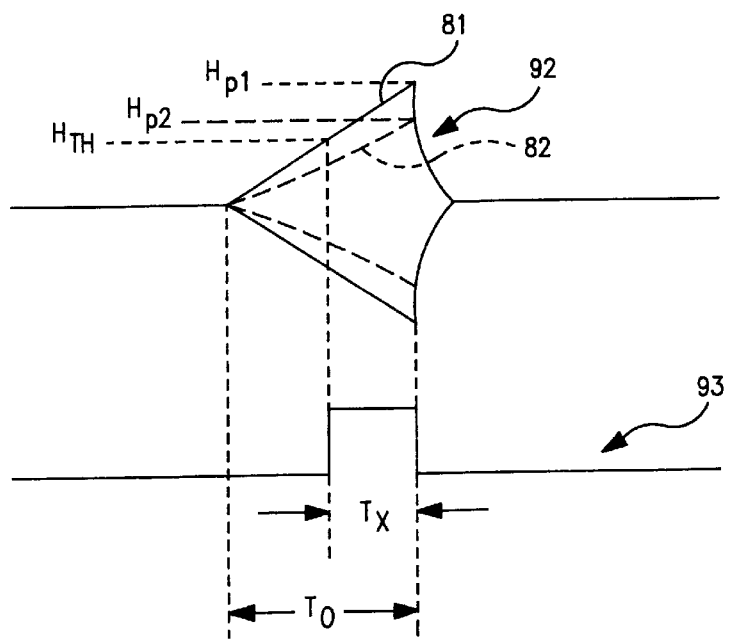

FIGS. 4A and 4B show embodiments of a prior art closed-loop downlink telemetry system as described in U.S. Pat. No. 5,324,315 to Grevious, entitled "Closed-Loop Downlink Telemetry and Method for Implantable Medical Device," issued Jun. 28, 1994. U.S. Pat. No. 5,324,315 describes a method of modulating the peak amplitude of downlink burst envelopes based upon information provided from an implantable medical device regarding the relative strength of detected downlink burst signals. As such, the external communication device can ensure an adequate margin over the implanted device's detection threshold while at the same time avoiding transmission of unnecessarily high energy downlink signals. The description of several aspects of U.S. Pat. No. 5,324,315 are provided herein as background to facilitate the description of the present invention as provided in further detail below with respect to FIGS. 5–8.

As shown in FIG. 4A, there is a stream of bursts 81, 82 for a downlink telemetry system. The modulation scheme used in FIG. 4A is once again trailing edge to trailing edge pulse interval modulation, as previously described herein with respect to FIG. 3D. As shown in FIG. 4A, a binary "1" is encoded as a shorter interval of duration $T_{L1}$ indicated by reference numeral 84 while a binary "0" is encoded as a longer interval of duration $T_{L0}$ indicated by reference numeral 86. However, unlike the bursts 184a–c shown in FIG. 3D, the envelope of the bursts in the downlink burst stream 80 include only a linear ramping portion of duration $T_0$. Further, as shown in FIG. 4A, each of the bursts 81, 82 is of the same burst duration $T_0$. However, downlink bursts 82 are provided with a lower peak amplitude $H_{p2}$, relative to the peak amplitude $H_{p1}$ of burst 81, resulting from a closed-loop control method for avoiding transmission of unnecessarily high energy downlink signals as described in U.S. Pat. No. 5,324,315.

FIG. 4B shows a burst envelope 92 illustrating the bursts 81, 82 from the burst stream of FIG. 4A. FIG. 4B further illustrates a detected downlink signal 93 representing the telemetry system signal derived by the downlink receiver from the burst envelope 92. Again, it is to be understood that the envelope 92 depicts an envelope for, preferably, a 175 kHertz burst that is transmitted from the external communication device's transmitter. In FIG. 4B, the dashed line $H_{th}$ represents the magnetic field threshold of the implantable medical device's downlink receiver circuitry. In other words, magnetic fields of magnetic magnitude less than $H_{th}$ are not received by the implantable medical device's downlink telemetry receiver. Accordingly, in the detected downlink signal 93 of FIG. 4B, it can be seen that the detected downlink signal has a duration $T_x$ which is less than the duration $T_0$ of the envelope 92. In particular, this occurs because the linear ramping envelope is such that the receiver threshold $H_{th}$ is not reached until some point after the start of the envelope 92.

Due to linearity of upward ramping in the envelope 92 of the downlink RF burst transmitted to the implantable medical device, the duration $T_x$ of the burst in the detected downlink signal 93 is directly proportional to the margin between the implantable medical device's receiver magnetic field threshold level $H_{th}$ and the maximum peak amplitude $H_p$ of the burst envelope. In particular, the detected downlink signal timing and the magnetic field strength are related according to the following equation (1):

$$T_x(H_{th}, H_p) = T_0\left(1 - \frac{H_{th}}{H_p}\right)$$

Given the foregoing relationship for an implanted downlink telemetry receiver having a known magnetic field sensitivity threshold $H_{th}$, the maximum amplitude of detected downlink telemetry pulses can be calculated once $T_x$ is known. In particular, the peak amplitude $H_p$ of the downlink telemetry burst envelopes as seen by the implanted downlink telemetry receiver is given by the following equation (2):

$$H_p = H_{th}\left(\frac{T_0}{T_0 - T_x}\right)$$

With such a relationship known, the downlink receiver of the implantable medical device decodes the detected downlink signal 93 to decode information regarding the length of the time interval $T_x$ for a received linear ramp downlink burst, such as burst 81. This time interval $T_x$ reflects the downlink signal strength as previously described, and a downlink strength signal can be issued. As described in U.S. Pat. No. 5,324,315, the downlink strength signal representative of the length of the $T_x$ interval is provided to the external communication device such that subsequent bursts, such as burst 82, may be modulated in amplitude as a function of the downlink strength signal. As such, for example, as shown in FIG. 4B, the peak amplitude $H_p$ may be modified from $H_{p1}$ for burst 81 to a peak amplitude $H_{p2}$ while still providing adequate margin over the detector threshold $H_{th}$. This reduces the total energy of the bursts 81, 82 relative to the bursts 184a–c used, for example, as described with reference to FIG. 3D.

Closed-loop control of downlink energy of bursts is addressed in U.S. Pat. No. 5,324,315 as described with reference to FIGS. 4A–4B herein. In U.S. Pat. No. 5,324,315, the measurement of $T_x$ provides a way of controlling the amplitude of the bursts transmitted by the external communication device, e.g., by adjusting the gain of the transmitter. However, the burst duration of each of the bursts is equivalent, i.e., $T_0$ is the same during the entire telemetry session. Only the peak amplitude of the bursts is modified to reduce energy transmitted, as clearly shown in FIGS. 4A and 4B.

According to the present invention, downlink energy control is also provided in a closed-loop manner. According to the present invention, such control is provided by the detection of one or more control bursts transmitted by the external communication device at a receiver of the implantable medical device. A downlink strength signal is generated representative of the strength of one or more control bursts detected at the implantable medical device's receiver. Thereafter, downlink data bursts from the external communication device are controlled as a function of the downlink strength signal. However, according to the present invention, the downlink bursts are not controlled by adjustment of peak amplitude of the envelope of the downlink bursts as described with reference to U.S. Pat. No. 5,324,315. Rather, energy control for downlink bursts in a downlink telemetry system according to the present invention is provided by adjustment of the burst duration of the downlink bursts transmitted by the external communication device as described further in detail below with respect to FIGS. 5–8.

By controlling the burst duration of the downlink data bursts and thereby reducing the peak amplitude and total energy for such bursts, a reduction of downlink magnetic field energy and electric field components is provided. Such a reduction in downlink magnetic field energy reduces, for example, inductive coupling of the magnetic field energy into a lead system of an implanted medical device such as a pacemaker lead system as described above. Further, an increase in downlink data rate may be provided by reducing maximum burst width, e.g., burst width below 150 μseconds. Such an increased downlink data rate shifts the rate away from energy bands monitored by sensing circuitry of the implantable medical device. For example, an increased downlink data rate from 1K baud to about 8K baud shifts energy away from an ECG sense amplifier band of a pacemaker.

Figure 5A:
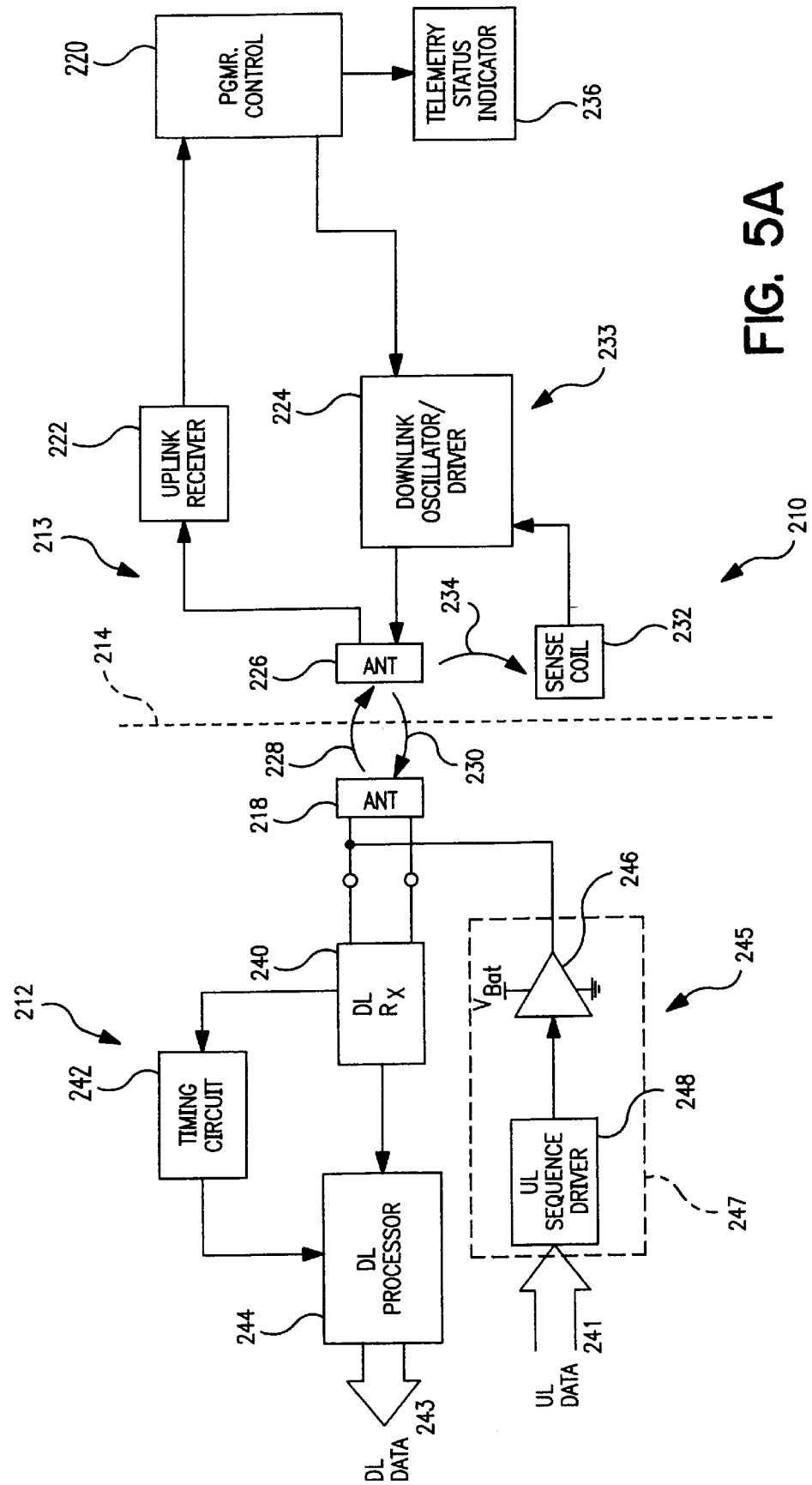
FIG. 5A is a block diagram of a downlink telemetry system according to the present invention.

FIG. 5A shows a block diagram of one embodiment of a downlink telemetry system 210 according to the present invention. The downlink telemetry system 210 includes implantable medical device 212 and external communication device 213. A dashed line 214 represents the boundary between implantable medical device 212 and external communication device 213. The implantable medical device 212 includes many components similar to those described with reference to FIG. 3, and the external communication device 213 also includes many components similar to those described with reference to FIG. 3. As such, the components previously described with reference to FIG. 3 shall not be described in further detail herein with respect to the telemetry system according to the present invention.

Implantable medical device 212 includes a telemetry subsystem 245 operable for receiving downlink data bursts and control bursts detected by antenna 218 and storing information encoded in such bursts. Further, the telemetry subsystem 245 is operable for providing uplink signals to antenna 218 for transmission to external communication device 213. The telemetry subsystem 245 includes various known components conventionally used in telemetry systems. For example, telemetry subsystem 245 includes a downlink receiver 240 and an uplink transmitter 247.

Generally, the downlink receiver 240 has a magnetic field detection threshold ($H_{th}$). In other words, magnetic fields of magnitude less than the detection threshold are not received by the downlink telemetry receiver 240. Downlink telemetry receiver 240 includes demodulation circuitry suitable for demodulating encoded data from the downlink burst stream to be provided to downlink processor 244. Processor 244 then uses the downlink data 243 as desired for a particular medical device, e.g., control pacing levels, program particular timing intervals for the device, etc. One skilled in the art will recognize that the function of some components may be carried out as part of a separate telemetry subsystem, i.e., separate from other functional components of the implantable medical device 212, or carried out by components of other functional systems of the implantable medical device 212, e.g., the processing may be performed by a single processor also used for processing cardiac waveforms.

Uplink transmitter 247 receives uplink data 241 for transmission to external communication device 213 at uplink sequence driver 248 of transmitter 247. Uplink sequence driver 248 provides for modulation of an uplink signal with the uplink data sequences. As previously described herein various modulation techniques may be used for uplink telemetry, and the present invention is not limited to any particular uplink telemetry technique. The uplink sequence driver 248 controls driver 246 to drive antenna 218 to communicate uplink data to external communication device 213, i.e., uplink receiver 222 via antenna 226.

External communication device 213 is preferably implemented as a microprocessor-based system, such as in the case of a Model 9710, 9760, or 9790 programming unit manufactured and commercially-available from Medtronic, Inc., the assignee hereof. The external communication device 213 includes programmer control circuitry 220 coupled to telemetry subsystem 233. Telemetry subsystem 233 includes uplink telemetry receiver 222 and downlink telemetry transmitter 224. Uplink telemetry receiver 222 includes demodulation circuitry corresponding to the modulation circuitry of transmitter circuitry 247 of the implantable medical device 212 for receiving an encoded uplink signal therefrom and demodulating the signal to provide information to the programmer control circuitry 220. Generally, the downlink transmitter 224 includes an oscillator and driver and is coupled to antenna 226 for transmission of RF bursts downlink to antenna 218.

Those of ordinary skill in the art will appreciate that antenna 226 is preferably disposed within a handheld programming head (not shown) so that the antenna may be conveniently placed above an implant site. When so positioned, antenna 226 receives uplink telemetry signals transmitted from implanted antenna 218, as indicated by arrow 228, and transmits downlink telemetry signals to be received by implanted antenna 218, as indicated by arrow 230. Further, external communication device 213 includes a sense coil 232 and telemetry status indicator 236 which function in a manner similar to that described herein with reference to FIG. 3.

Figure 5B:
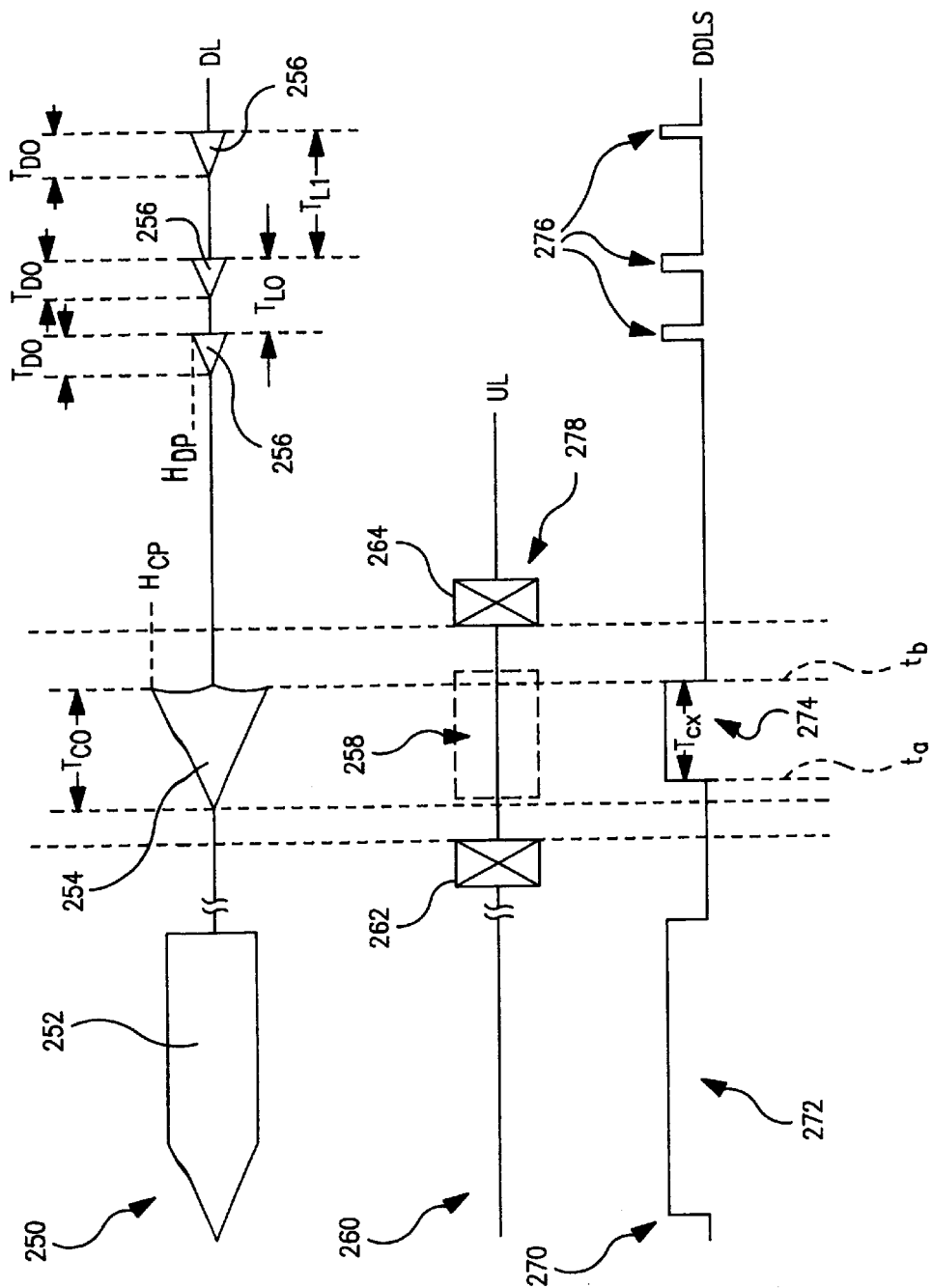
FIG. 5B is an illustration for use in describing energy control of downlink telemetry for the downlink telemetry system of FIG. 5A.

The operation of the downlink telemetry system 210 according to the present invention is further best described with reference to downlink and uplink telemetry signals communicated between the implantable medical device 212 and external communication device 213. As shown in FIG. 5B, downlink burst stream (DL) 250 is transmitted by external communication device 213 downlink to implantable medical device 212. The downlink burst stream 250 includes a wake-up pulse 252 for initiating a telemetry session. As previously described herein, other methods of initiating the telemetry session may be used according to the present invention. For example, closure of a reed switch to initiate the telemetry session may be used or downlink receiver polling for a wake-up burst may be used. FIG. 5B further includes an uplink telemetry signal (UL) 260 which includes at least handshake protocol information. Yet further, FIG. 5B includes detected downlink signal (DDLS) 270 which reflects pulses representative of detected bursts of burst stream 250. For example, pulse 272 reflects the detection of wakeup burst 252. It will be recognized that the detected downlink signal waveform 270 will include pulses such as pulse 272 which are of a duration less than the corresponding burst 252 which is detected due to the detection threshold ($H_{th}$) of the implanted medical device downlink receiver 240 as previously described herein.

Upon initiation of a telemetry session by any suitable wakeup technique, telemetry system 210 performs a handshake protocol so as to ensure continuous maintenance of uplink and/or downlink channels for use in conjunction with the present invention. Such a handshake protocol may take any number of forms. Preferably, the handshake protocol is a protocol substantially like the protocol described herein with reference to FIGS. 3B and 3C. Such a protocol is shown in FIG. 5E wherein a handshake sequence 278 is periodically performed to ensure suitable links.

Figure 5C:
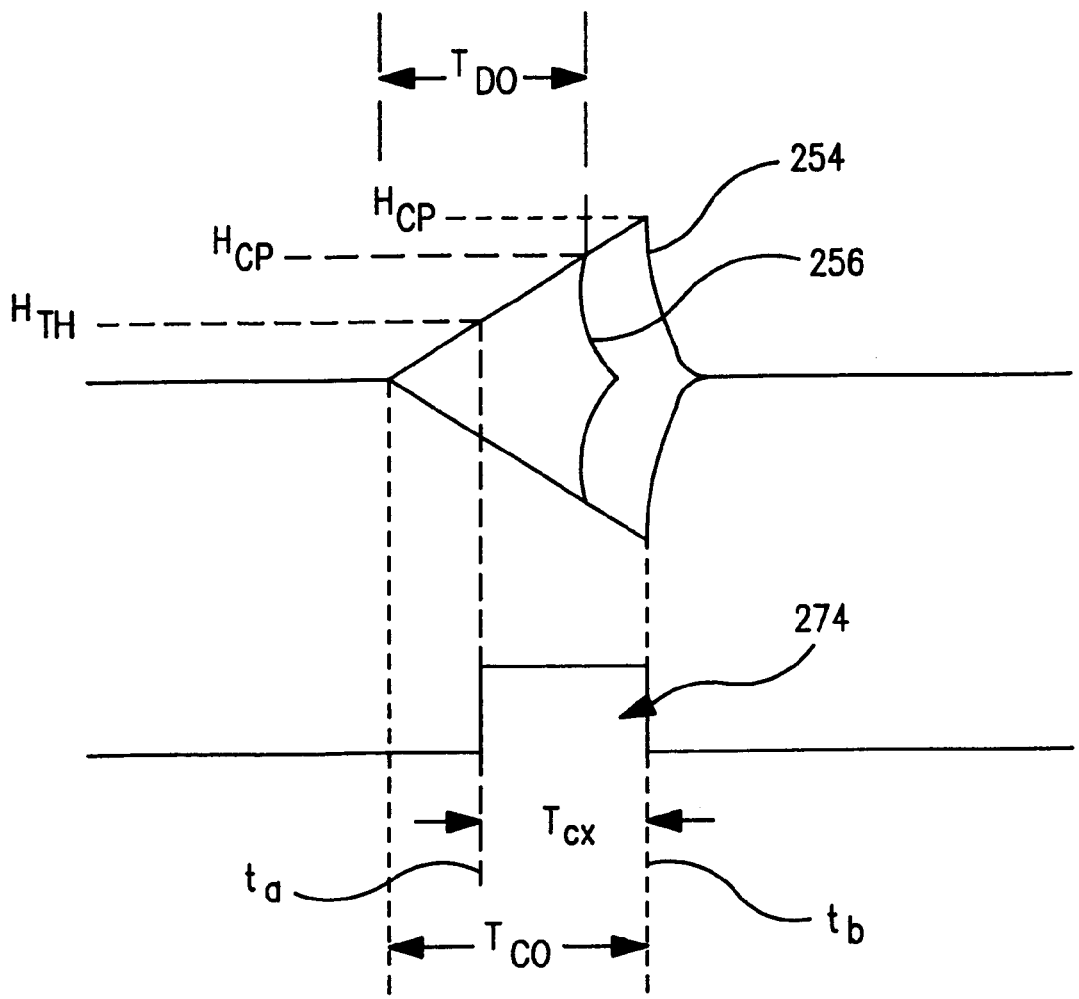
FIG. 5C is an illustration of a downlink control burst for use in describing energy control of downlink telemetry for the downlink telemetry system of FIG. 5A.
Figure 5D:
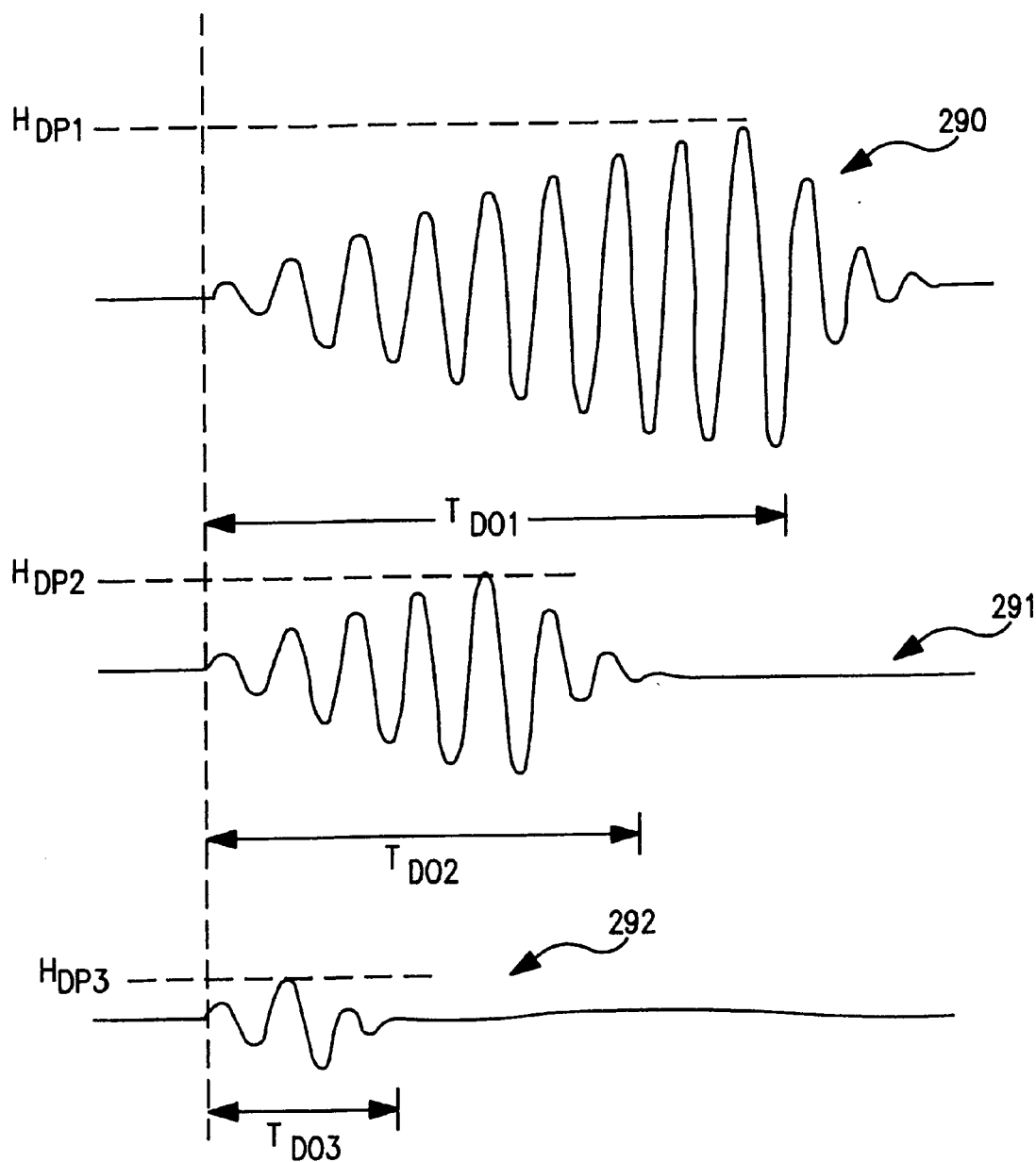
FIG. 5D is an illustration of RF bursts having different burst durations according to the present invention.
Figure 5E:
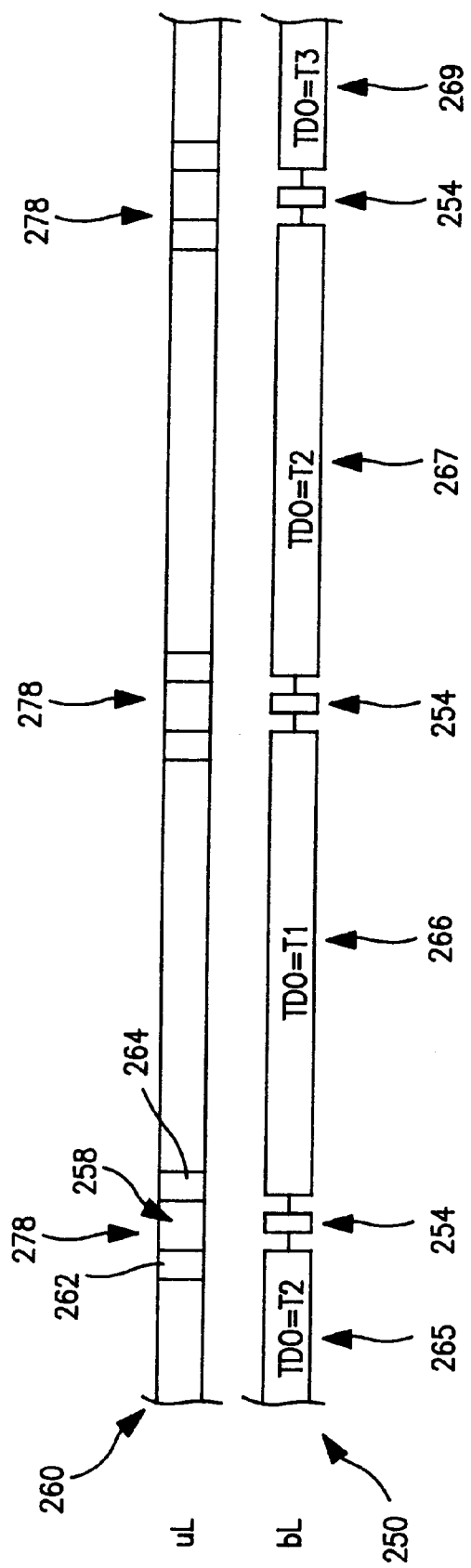
FIG. 5E is an illustration for use in describing energy control of downlink telemetry according to the present invention, such as, for example, with use of the telemetry system of FIG. 5A.

As shown in the uplink telemetry signal 260 of FIG. 5E and FIG. 5B, each periodically performed handshake sequence 278 includes a handshake request 262, a handshake reply window 258, and a handshake confirmation 264. In this particular illustrative embodiment, the handshake request 262 is transmitted uplink from the implantable medical device transmitter 247. A handshake reply from the external communication device 213 is then awaited during the handshake reply window 258. According to one embodiment of the present invention, when a handshake request is detected by uplink receiver 222 of external communication device 213, a single downlink control burst 254 is transmitted downlink in the downlink burst stream 250 by transmitter 224 of external communication device 213 under control of program control circuitry 220.

Generally, the downlink control burst 254 is defined by a ramped envelope having a burst duration $T_{CO}$ and a peak amplitude $H_{CP}$ as shown in FIG. 5C. Generally, the ramped envelope of downlink telemetry signals are bursts of radio frequency oscillating signal. Preferably, according to the present invention, the downlink bursts are bursts of a 175 kHertz oscillating signal.

As shown in FIG. 5B, the downlink receiver 240 of implantable medical device 212 provides for the detection of the downlink control burst 254 within the handshake window 258. The detected downlink pulse 274 is representative of the detected control burst 254. The duration $T_{CX}$ of detected downlink pulse 274 is generally the time interval from the time $t_a$ when the RF burst 254 is ramped to a level which exceeds the detection threshold ($H_{th}$) of the downlink telemetry receiver 240 to the time $t_b$ when the burst at the trailing edge falls to below the threshold $H_{th}$. Generally, the trailing edge falls very quickly and $t_b$ is very similar to the time when the burst reaches its peak amplitude $H_p$. As would be understood by one skilled in the art, delays between the transmitted and received signals may occur which are controlled by commonly known design methods and as such are not addressed herein. Upon detection of the downlink control burst 254 by the downlink receiver 240, telemetry system 245 provides for communication of a handshake confirmation 264 to external communication device 213.

As shown in FIG. 5B, and generally in FIG. 5E, after a handshake sequence 278 has established a functional downlink channel, downlink data bursts 256 are provided which are modulated with data. Generally, the downlink data bursts 256 are each defined by a ramped envelope having a burst duration $T_{DO}$ and a peak amplitude $H_{DP}$ as shown in FIG. 5B. Preferably, the ramped envelope of downlink telemetry signals are bursts of radio frequency oscillating signal just like the control burst 254. Preferably, according to the present invention, the downlink data bursts are bursts of a 175 kHertz oscillating signal.

It is an object of the present invention to control the total downlink energy of the downlink data bursts 256 by adjusting the burst duration of the downlink bursts as a function of the strength of one or more detected downlink control bursts, e.g., in this embodiment, the detection of a single control burst 254 represented by a corresponding detected downlink pulse 274. Preferably, according to the present invention, the burst duration $T_{DO}$ of the downlink data bursts is adjustable within the range of about 5 µseconds to about 150 µseconds, more preferably within the range of about 10 µseconds to about 100 µseconds, and most preferably within a range of about 10 µseconds to about 50 µseconds.

Illustrative bursts are shown in FIG. 5D. Burst 290 has a burst duration of $T_{DO1}$, burst 291 has a burst duration of $T_{DO2}$, and burst 292 has a burst duration of $T_{DO3}$. Generally, as the burst duration decreases, from $T_{DO1}$ to $T_{DO3}$, the peak amplitude also decreases from $H_{DP1}$ to $H_{DP3}$, according to the ramped nature of the burst. As such, according to the present invention, by adjusting the burst duration, peak amplitude can be adjusted as well as total energy of the downlink burst. The present invention leverages the ramp up of the burst as the useable adjustable range for controlling energy of downlink bursts. The present invention relies on a ramping of the burst from origination to a peak amplitude. The ramping of the burst envelope need not be completely linear in nature. However, preferably, the ramping of the envelope is a generally linear ramping envelope. The maximum error in linearity of the ramping of the burst envelope which would be reasonable according to the present invention and still provide suitable energy control would be an error in linearity that would result in a threshold margin error of less than about 3 dB.

In accordance with this embodiment of the telemetry system 210 shown in FIG. 5A, direct measurement of $T_{CX}$ for the downlink control burst 254 is determined such that the burst duration $T_{DO}$ of downlink data bursts 256 can be set as a function thereof. The duration of $T_{CX}$ is measured by timing the interval between time $t_a$ and time $t_b$ using timing circuitry 242 (see FIG. 5A). Such timing circuitry 242 would require a suitable clock speed in the implantable medical device 212, such that timing measurements with a resolution no worse than, for example, 5 µsecond, could be attained. This direct $T_{CX}$ measurement represented by the time interval between $t_a$ and $t_b$ is provided to downlink processor 244 resulting in a downlink strength signal representative of the strength of the downlink control burst 254 received at the receiver 240 of the implantable medical device 212. The downlink strength signal is then provided as uplink information 241 to transmitter 247 for uplink telemetry to external communication device 213. External communication device 213 can then use this downlink strength signal representative of the strength of the downlink control burst received at the receiver of implantable medical device 212 to adjust the burst duration $T_{DO}$ of downlink data bursts 256 to be transmitted thereby.

The burst duration $T_{DO}$ to be used for transmission of downlink data bursts 256 is determined by program control circuitry 220 of external communication device 213 upon receipt of the downlink strength signal representative of the time interval $T_{CX}$. The program control circuitry 220 calculates the burst duration $T_{DO}$ so as to achieve a desired operating margin, preferably at least 3 dB and more preferably at least 6 dB.

The operating margin, represented by the $H_p/H_{th}$ ratio, is set such that if the antenna 226 or patient moves slightly during downlink telemetry, the downlink channel will not fail. The operating margin will vary depending upon various factors. For example, the $H_p/H_{th}$ ratio may generally be chosen as a function of the handshake interval time, i.e., the time period between handshake sequences 278. The longer the handshake interval time, the larger the margin. For example, a 6 dB operating margin may be appropriate for a 250 millisecond handshake interval time. For slower programmer head motion, generally good tracking is attainable at longer handshake interval times and larger $H_p/H_{th}$ margins.

A calculation is performed by the programmer control circuitry 220 to arrive at the burst duration $T_{DO}$ to be used for transmission of downlink data bursts 256. Generally, $H_p/H_{th}=T_{DO}/T_{CX}$. In other words, the burst duration $T_{DO}$ for the downlink data bursts 256 is set at the desired operating margin ($H_p/H_{th}$) multiplied by the time interval $T_{CX}$ of the detected control pulse. For example, to achieve a 6 dB margin condition, $T_{DO}$ would equal $2T_{CX}$. As shown in FIG. 5B, the burst duration for downlink data bursts 256 is provided at a decreased level relative to downlink control burst 254. Further, as shown by the detected downlink signal 270, each of the downlink data bursts 256 were detected by the receiver 240 as shown by the detected downlink pulses 276.

The downlink control burst 254 may be transmitted at a burst duration within the ranges established above for downlink data bursts 256. Preferably, for example, the downlink control burst 254 in a handshake sequence may be transmitted at the same burst duration as a preceding downlink data burst was transmitted thus maintaining the desired characteristics explained previously. The first control burst of a telemetry session (or if a handshake fails, then the next downlink control burst 254) is transmitted at a maximum burst duration such that a maximum peak amplitude is attained for the control burst. In this manner, it is more likely that the control burst of maximum duration will be detected by the receiver 240 of the implanted medical device.

Preferably, uplink telemetry of the direct measurement of $T_{CX}$ to the external communication device 213 may be performed by providing the downlink strength signal representative thereof in the handshake confirmation 264 of a handshake sequence 278. As shown in FIG. 5E and as previously described herein, handshake sequences 278 are periodically carried out during the telemetry session. Between handshake sequences 278, as described above, downlink data bursts 256 are provided which are modulated with data. As such, and as shown in FIG. 5E, energy control can be adjusted at each handshake sequence 278 in a manner as described above. For example, as generally shown in downlink burst stream 250, downlink data bursts during time period 265 are provided at a burst duration of $T_2$. Thereafter, handshake 278 is performed using a downlink control burst 254 (e.g., a control burst having a maximum burst duration or a burst duration equivalent to preceding downlink data bursts) and an adjustment to the burst duration of downlink data bursts is performed as a function of the detected downlink strength of the received control burst. The burst duration for transmission of downlink data bursts during the time period 266 after the handshake sequence 278 is then $T_1$. Likewise, after the next handshake, burst duration $T_{DO}$ for the transmitted downlink data bursts in time period 267 is determined by the preceding handshake and is $T_2$. The burst duration determined during a handshake is preferably used for an entire time period between handshake sequences ending with the next handshake request by the implantable medical device. This is currently illustrated in FIG. 5E by the use of $T_{DO}=T_2$ during a first time period 265, the use of $T_{DO}=T_1$ during a second time period 266, the use of $T_{DO}=T_2$ during time period 267, and the use of $T_{DO}=T_3$ during time period 269. Each of the time periods extend between handshake sequences 278.

As shown in FIG. 5B, the downlink data bursts 256 are modulated with data using pulse interval modulation with respective different intervals representing 0's and 1's as previously described herein. As will be recognized from the description herein, pulse width modulation and pulse position modulation may also be used to encode the downlink data bursts 256.

Figure 6A:
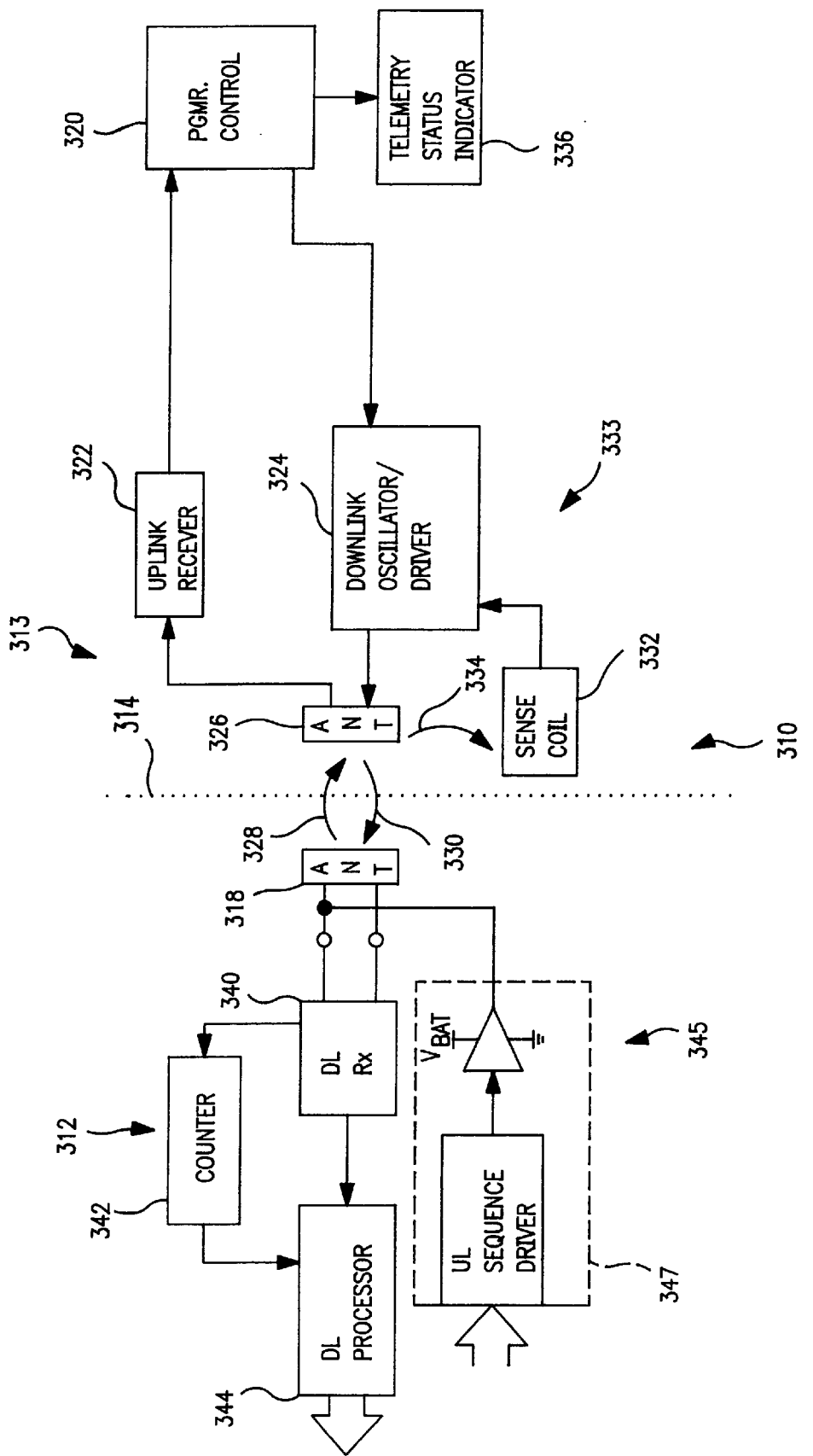
FIG. 6A is an alternate embodiment of a downlink telemetry system according to the present invention.

FIG. 6A shows a block diagram of another embodiment of a downlink telemetry system 310 according to the present invention. The downlink telemetry system 310 includes implantable medical device 312 and external communication device 313. A dashed line 314 represents the boundary between implantable medical device 312 and external communication device 313. The implantable medical device 312 includes many components similar to those described with reference to FIG. 3 and FIG. 5A, and the external communication device 313 also includes many components similar to those described with reference thereto. As such, the components previously described with reference to such Figures shall not generally be described in further detail herein with respect to the telemetry system 310 of FIG. 6A.

Implantable medical device 312 includes a telemetry subsystem 345 operable for receiving downlink data bursts and control bursts detected by antenna 318 and storing information encoded in such bursts. Further, the telemetry subsystem 345 is operable for providing uplink signals to antenna 318 for transmission to external communication device 313. The telemetry subsystem 345 includes various known components conventionally used in telemetry systems. For example, telemetry subsystem 345 includes a downlink receiver 340 and an uplink transmitter 347.

Generally, the downlink receiver 340 has a magnetic field detection threshold ($H_{th}$). Further, downlink telemetry receiver 340 includes demodulation circuitry suitable for demodulating encoded data from the downlink burst stream to be provided to downlink processor 344 for use as desired for a particular medical device. Uplink transmitter 347 receives uplink data for transmission to external communication device 313.

External communication device 313 is preferably implemented as a microprocessor-based system, such as in the case of a Model 9710, 9765, or 9790 programming unit manufactured and commercially-available from Medtronic, Inc., the assignee hereof. The external communication device 313 includes programmer control circuitry 320 coupled to telemetry subsystem 333. Telemetry subsystem 333 includes uplink telemetry receiver 322 and downlink telemetry transmitter 324. Further, external communication device 313 includes a sense coil 332 and telemetry status indicator 336.

Figure 6B:
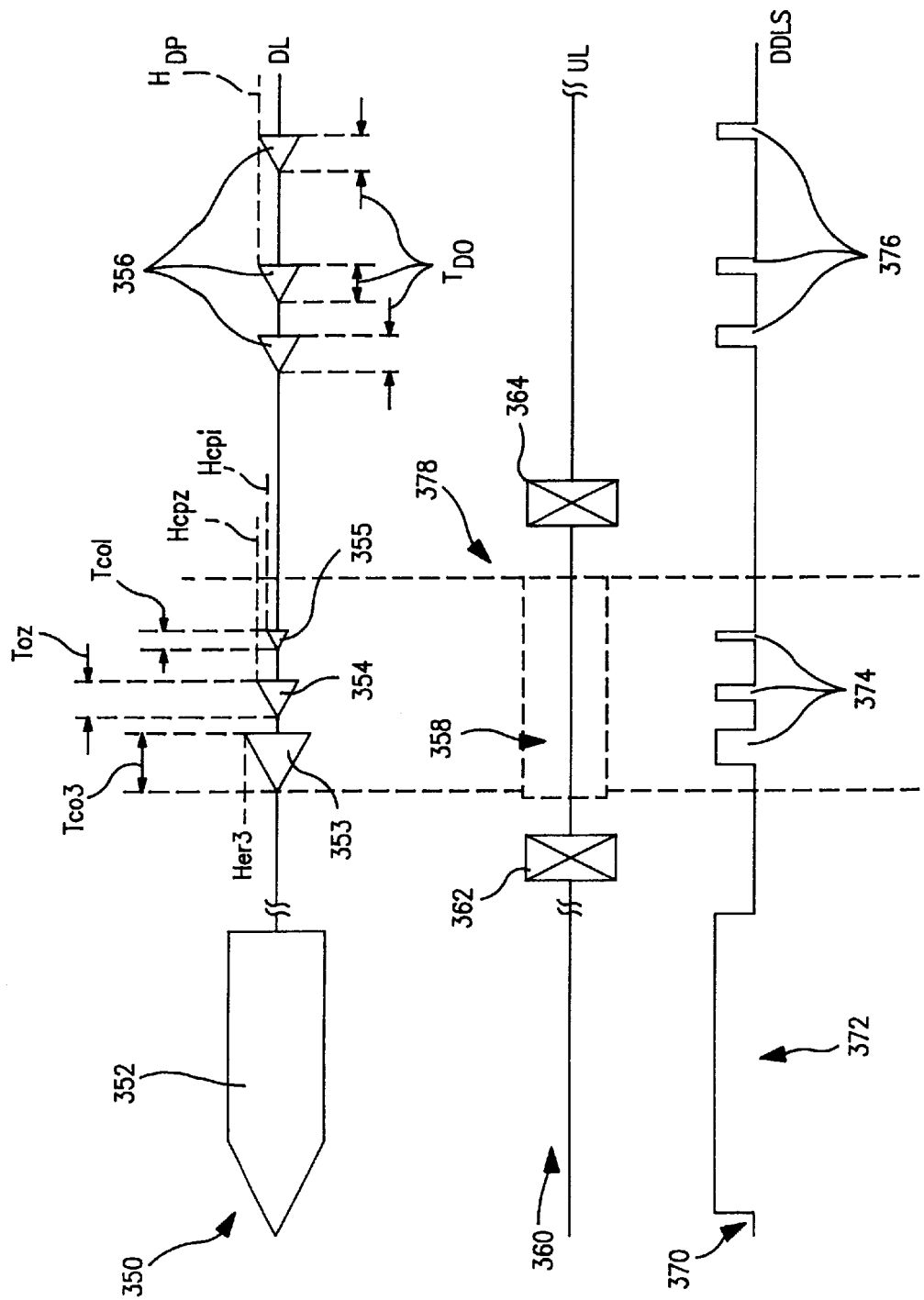
FIG. 6B is an illustration for use in describing energy control for downlink telemetry using the system of FIG. 6A.

The operation of the downlink telemetry system 310 according to the present invention is further best described with reference to downlink and uplink telemetry signals communicated between the implantable medical device 312 and external communication device 313 as shown in FIG. 6B. In FIG. 6B, downlink burst stream (DL) 350 is transmitted by external communication device 313 downlink to implantable medical device 312. The downlink burst stream 350 includes a wake-up pulse 352 for initiating a telemetry session. As previously described herein, other methods of initiating the telemetry session may be used according to the present invention. FIG. 6B further includes an uplink telemetry signal (UL) 360 which includes at least handshake protocol information. Yet further, FIG. 6B includes detected downlink signal (DDLS) 370 which reflects pulses representative of detected bursts of burst stream 350. For example, pulse 372 reflects the detection of wakeup burst 352.

Upon initiation of a telemetry session by any suitable wakeup technique, telemetry system 310 performs a handshake protocol so as to ensure continuous maintenance of uplink and/or downlink channels for use in conjunction with the present invention. Such a handshake protocol may take any number of forms. Preferably, the handshake protocol is a protocol substantially like the protocol described herein with reference to FIGS. 3B and 3C and as described with reference to FIGS. 5A–5E. The handshake sequence 378 is periodically performed to ensure suitable links.

As shown in the uplink telemetry signal 360 of FIG. 6B, each periodically performed handshake sequence 378 includes a handshake request 362, a handshake reply window 358, and a handshake confirmation 364. In this particular illustrative embodiment, the handshake request 362 is transmitted uplink from the implantable medical device transmitter 347. A handshake reply from the external communication device 313 is then awaited during the handshake reply window 358. According to this embodiment of the present invention, when a handshake request is detected by uplink receiver 322 of external communication device 313, a predetermined number of downlink control bursts 353–355 are transmitted downlink in the downlink burst stream 350 by transmitter 324 of external communication device 313 under control of program control circuitry 320.

Generally, the predetermined number of downlink control bursts 353–355 are each defined by a ramped envelope. Each of the control bursts 353–355 have a different respective burst duration $T_{CO1}$–$T_{CO3}$ and as such different respective peak amplitudes $H_{CP1}$–$H_{CP3}$ as shown in FIG. 6B. Preferably, the difference between the peak amplitude of one downlink control burst to the next subsequent downlink control burst is equal to a desired minimum operating margin. For example, as shown in FIG. 6B, if the desired operating margin is 6 dB, then the peak amplitude $H_{CP1}$ of control burst 353 set by the burst duration $T_{CO1}$ is 6 dB greater than the peak amplitude $H_{CP2}$ of control burst 354 set by the burst duration $T_{CO2}$. Likewise, the peak amplitude $H_{CP2}$ of control burst 354 set by the burst duration $T_{CO2}$ is 6 dB greater than the peak amplitude $H_{CP3}$ of control burst 354 set by the burst duration $T_{CO3}$. Generally, the ramped envelopes of downlink telemetry signals are bursts of radio frequency oscillating signal. Preferably, according to the present invention, the downlink bursts are bursts of a 175 kHertz oscillating signal.

As shown in FIG. 6B, the downlink receiver 340 of implantable medical device 312 provides for the detection of one or more of the downlink control bursts 353–355 within the handshake window 358. In one embodiment, a preferred detector is a detector that produces a full wave rectification of the received signal. The number of downlink control bursts detected, i.e., the number of downlink pulses 374 in detected downlink signal 370, is representative of the strength of the detected signal received by the receiver 340 of the implanted medical device 312 from the external communication device 313. The number of detected bursts, i.e., the count of pulses 374, is generally a count of the number of control bursts which exceed the detection threshold ($H_{th}$) of the downlink telemetry receiver 340. Upon detection and count of the number of control bursts which exceed the detection threshold ($H_{th}$) by the downlink receiver 340 and associated circuitry, telemetry system 345 provides for communication of a handshake confirmation 364 to external communication device 313.

As shown in FIG. 6B after a handshake sequence 378 has established a functional downlink channel, downlink data bursts 356 are provided which are modulated with data. Generally, the downlink data bursts 356 are each defined by a ramped envelope having a burst duration $T_{DO}$ and a peak amplitude $H_{DP}$ as shown in FIG. 6B. Preferably, the ramped envelope of downlink telemetry signals are bursts of radio frequency oscillating signal just like the control burst 254. Preferably, according to the present invention, the downlink data bursts are bursts of a 175 kHertz oscillating signal.

Figure 6C:
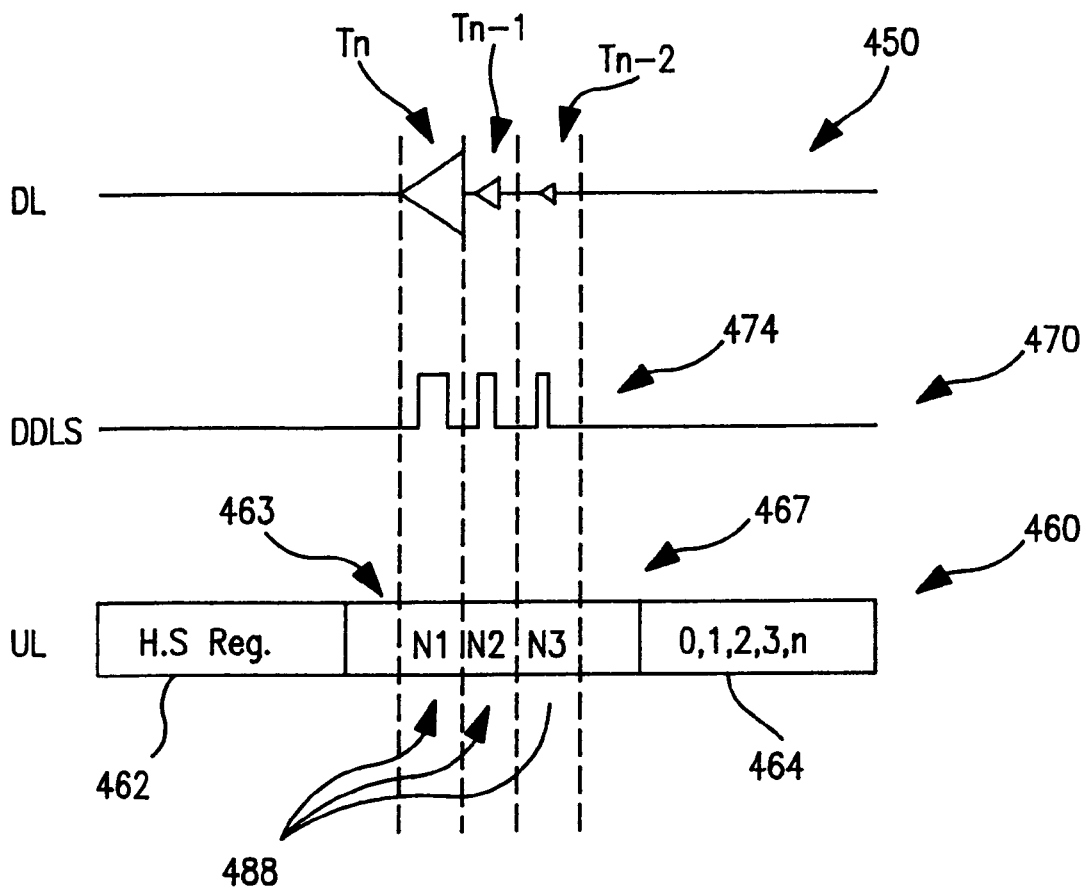
FIG. 6C is a general diagram for further illustrating energy control of downlink telemetry according to the present invention using the downlink telemetry system of FIG. 6A.

It is an object of the present invention according to this embodiment to control the total downlink energy of the downlink data bursts 356 by adjusting the burst duration of the downlink bursts as a function of the strength of detected downlink control bursts. In this embodiment, the strength of detected downlink control bursts is represented by the count of detected downlink pulses, e.g., pulses 374. Preferably, according to the present invention, the burst duration $T_{DO}$ of the downlink data bursts is adjustable within the range of about 5 $\mu$seconds to about 150 $\mu$seconds, more preferably within the range of about 10 $\mu$seconds to about 100 $\mu$seconds, and most preferably within a range of about 10 $\mu$seconds to about 50 $\mu$seconds. However, unlike the control of burst duration described with reference to the embodiment of FIGS. 5A–5E wherein the burst duration of the downlink data bursts fall anywhere within the ranges given above, burst duration for downlink data bursts according to this embodiment described with reference to FIGS. 6A–6C is chosen from a predetermined number of discrete burst duration times falling within the ranges given above. Preferably, the discrete burst durations are of the same duration as the downlink control bursts. This embodiment still leverages the ramp up of the burst as the useable adjustable range for controlling energy of downlink bursts; preferably, a generally linear ramping envelope.

In accordance with this embodiment of the telemetry system 310 shown in FIG. 6A, the strength of the detected downlink control bursts is determined by counting the number of control bursts 353–355 which are detected by the receiver 340, i.e., detection of those bursts which exceed the detection threshold of the receiver 340. The burst duration of the downlink data bursts 356 is chosen dependant upon the count of the detected control bursts 353–355. Generally, the burst duration $T_{DO}$ selected for the downlink data bursts 356 is the burst duration that is one operating margin greater than the smallest burst detected. As such, the energy of downlink data bursts 356 exceed the detection threshold of the downlink receiver by at least one operating margin. For example, as shown in FIG. 6B and assuming that the three control bursts 353–355 are separated from each other by an operating margin of 6 dB, if all three of the control bursts 353–355 are detected as shown by detected downlink pulses 374, then the burst duration $T_{DO}$ for the downlink data bursts 356 would be selected as $T_{CO2}$. This assures that the downlink data bursts 356 are transmitted at least 6 dB over the smallest control burst 355 detected which is separated from control burst 354 by a 6 dB operating margin.

The number of control bursts detected is determined using counter 242 (see FIG. 6A). The counter 242 is an easily implemented circuit, e.g., count on a falling edge of a burst, which provides advantages over the embodiment described herein with reference to FIGS. 5A–5E. For example, no time interval or pulse width measurement needs to be determined as is required in the embodiment of FIGS. 5A–5E. This count of control bursts representative of the strength of downlink signals received at the receiver 340 of the implantable medical device 312, is then provided as uplink information to transmitter 347 for uplink telemetry to external communication device 313. External communication device 313 can then use this downlink strength signal representative of the count of downlink control bursts received at the receiver of implantable medical device 312 to adjust the burst duration $T_{DO}$ of downlink data bursts 356 to be transmitted thereby.

The burst duration $T_{DO}$ to be used for transmission of downlink data bursts 356 is determined by program control circuitry 320 of external communication device 313 upon receipt of the downlink strength signal representative of the count of control bursts detected. The program control circuitry 320 may for example, include a look up table which selects a particular burst duration $T_{DO}$ depending upon the count received from the implanted medical device 312. As shown in FIG. 6B, the burst duration for downlink data bursts 356 is provided at a decreased level relative to downlink control burst 353. Further, as shown by the detected downlink signal 370, each of the downlink data bursts 356 were detected by the receiver 340 as shown by the detected downlink pulses 376.

The above embodiment was described with reference to the use of three control bursts 353–355. However, as shown generally in FIG. 6C, the above discrete burst duration control of downlink data bursts can be implemented using any number of downlink control bursts 450 represented by the burst durations $T_n$. As shown in FIG. 6C, each of the downlink control bursts 450 is transmitted in a corresponding nibble position ($N_1$–$N_3$) of the handshake reply window 463 following the receipt of a handshake request 462 of a handshake sequence 461. The count of the detected control bursts as represented in the detected downlink signal 470 by pulses 474 is then provided in the handshake confirmation 464.

Generally, the burst duration for the control bursts is provided by the following general equation: $T_n = T_1/B^{(n-1)}$, where B represents the operating margin, e.g., B=2 for an operating margin of +/−6 dB, 1.414 for +/−3 dB, etc., and further where $T_1$ is a burst duration resulting in a burst having a maximum peak amplitude. For example, for a five control burst embodiment with B=2, control pulses having burst durations of $T_1$, $T_1/2$, $T_1/4$, $T_1/8$, and $T_1/16$, would be provided. Preferably, five or less downlink control bursts are used; more preferably, three downlink control bursts are used.

Preferably, the same discrete burst durations used for the control bursts are used when selecting the burst duration $T_{DO}$ for the downlink data bursts as a function of the count of detected control bursts. For example, for the five control burst embodiment with B=2, when the count is 0 then the handshake has failed and maximum duration $T_1$ is used, when the count is 1 then $T_1$ is used for $T_{DO}$, when the count is 2 then $T_1$ is used for $T_{DO}$, when the count is 3 then $T_1/2$ is used for $T_{DO}$, when the count is 4 then $T_1/4$ is used for $T_{DO}$, and when the count is 5 then $T_1/8$ is used for $T_{DO}$.

Preferably, uplink telemetry of the count of detected control bursts to the external communication device 313 may be performed by providing the downlink strength signal representative of the count in the handshake confirmation 364 of a handshake sequence 378. As previously described herein, handshake sequences 378 are periodically carried out during the telemetry session and therefore, energy control can be adjusted at each handshake sequence 378 according to the count of detected control bursts at each handshake sequence.

As shown in FIG. 6B, the downlink data bursts 356 are modulated with data using pulse interval modulation with respective different intervals representing 0's and 1's as previously described herein. As will be recognized from the description herein, pulse width modulation and pulse position modulation may also be used to encode the downlink data bursts 356 as further described below.

Figure 7A:
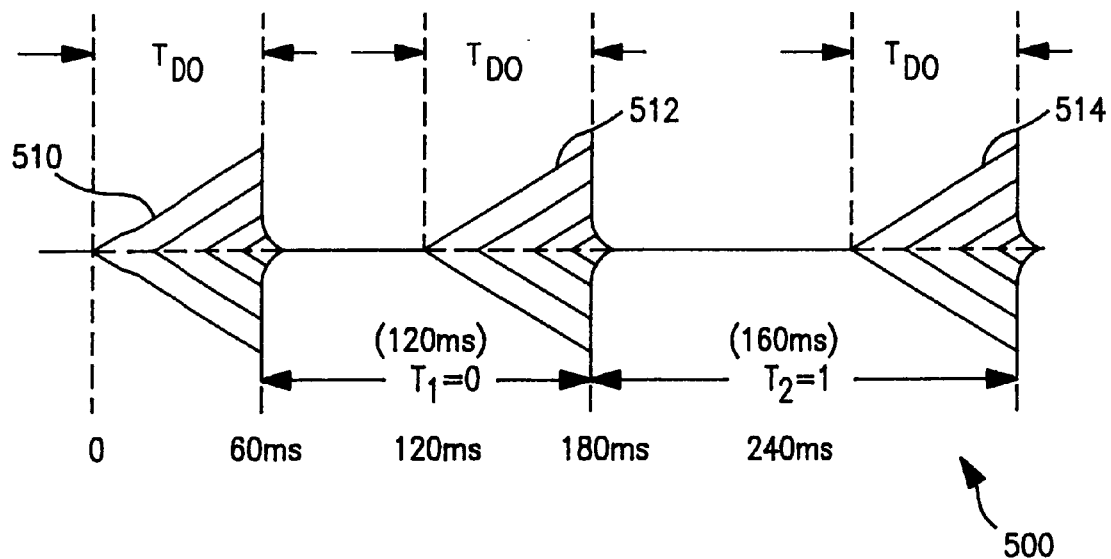
FIGS. 7A–7B is an illustration showing downlink energy control according to the present invention in conjunction with a combination pulse position and pulse width modulation of downlink data bursts.
Figure 7B:
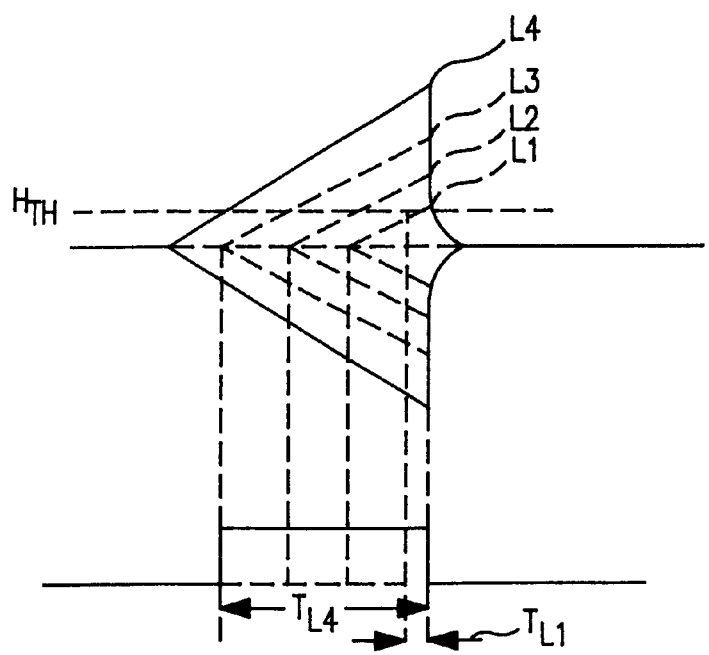
Figure 8:
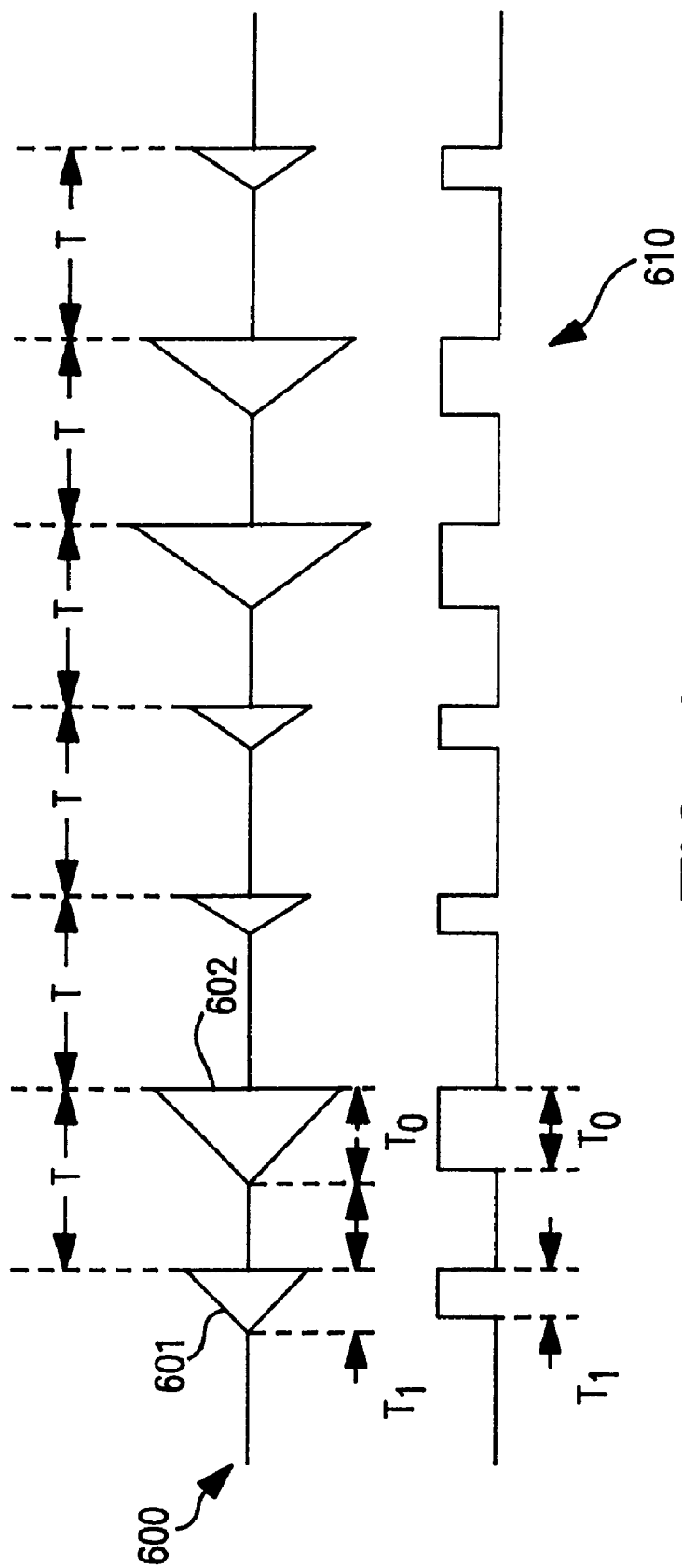
FIG. 8 is an illustration showing downlink energy control according to the present invention in combination with two level burst width modulation according to the present invention.

FIGS. 7 and 8 show embodiments of the present invention where modulation techniques different than simply pulse interval modulation are used for modulating downlink data burst streams in conjunction with the downlink energy control techniques described above. As shown in the burst stream 500 of FIG. 7A, pulse position and pulse width modulation are combined to yield one octal byte per interval. For example, the interval defined by the burst trailing edges defines one binary bit of encoding, e.g., $T_1$ from the trailing edge of burst 510 to the trailing edge of burst 512 is a zero and $T_2$ from the trailing edge of burst 512 to the trailing edge of 514 is a one. The detected burst width of FIG. 7B representative of four discrete levels (L1–L4) define two additional binary bits, e.g., $T_{L4}=11$ and $T_{L1}=00$. As shown, each bursts 510, 512, 514 is of equivalent duration $T_{DO}$.

FIG. 8 depicts a two level burst width modulation encoding technique. The bursts occur at fixed intervals (T) in burst stream 600. For this implementation, the width of burst 601 ($T_1$) is established per the techniques for energy control as described above. The width of burst 602 ($T_0$) is increased by amount deemed suitable to distinguish a $T_1$ burst from a $T_0$ burst. The detected burst widths ($T_1'$ and $T_0'$) of downlink detected signal 610 are assigned a binary value based on the measurement of a reference burst elsewhere in the protocol such as a start bit used to mark the beginning of data. A reference burst width can also be established during the last handshake used to establish the operating burst width for downlink data transmission.

All patents and references cited herein are incorporated in their entirety as if each were incorporated separately. This invention has been described with reference to illustrative embodiments and is not meant to be construed in a limiting sense. As described previously, one skilled in the art will recognize that various other illustrative applications may utilize the downlink telemetry system according to the present invention. Various modifications of the illustrative embodiments, as well as additional embodiments of the invention, will be apparent to persons skilled in the art upon reference to this description.

What is claimed is:

1. An implantable medical device telemetry method for downlink transmission of telemetry signals between a transmitter of an external communication device and a receiver of an implantable medical device, the method comprising the steps of:
   providing one or more downlink control bursts from the transmitter, wherein each downlink control burst is defined by a ramped envelope having a burst duration and a peak amplitude;
   detecting one or more of the downlink control bursts received at the receiver of the implanted medical device from the transmitter and generating a downlink strength signal representative of the strength of the one or more downlink control bursts;
   providing a plurality of downlink data bursts from the transmitter, wherein the plurality of downlink data bursts are modulated with data, and further wherein each downlink data burst is defined by a ramped envelope having a burst duration and a peak amplitude; and
   controlling the peak amplitude of the plurality of downlink data bursts by adjusting the burst duration of the ramped envelope as a function of the downlink strength signal.

2. The method of claim 1, wherein the step of providing the one or more downlink control bursts includes:
   providing at least one handshake between the external communication device and implantable medical device; and
   providing the one or more control bursts during the at least one handshake between the external communication device and implantable medical device.

3. The method of claim 2, wherein the step of providing the at least one handshake includes:
communicating a handshake request uplink from a transmitter of the implantable medical device to a receiver of the external communication device;
transmitting the one or more downlink control bursts from the transmitter of the external communication device to the receiver of the implantable medical device in response to the handshake request; and
communicating the downlink strength signal in a handshake confirmation from the transmitter of the implantable medical device to the external communication device.

4. The method of claim 2, wherein providing the one or more control bursts includes providing at least a first handshake and a second handshake between the external communication device and the implantable medical device, wherein said plurality of downlink data bursts are transmitted between the first and second handshakes, and wherein the one or more downlink control bursts are provided during at least the first handshake;
wherein the step of detecting one or more of the downlink control bursts includes detecting one or more of the downlink control bursts during the first handshake and generating a downlink strength signal as a function thereof; and
further wherein the step of controlling the peak amplitude includes controlling the peak amplitude of the plurality of downlink data bursts transmitted during the time between the first and second handshakes by adjusting the burst duration of the ramped envelope as a function of the downlink strength signal.

5. The method of claim 1, wherein the step of providing one or more downlink control bursts includes providing a single downlink control burst, and further wherein the step of detecting one or more of the downlink control bursts includes:
receiving the single downlink control burst signal by the receiver, wherein the receiver has a detected signal threshold;
determining the time interval during which the single downlink control burst exceeds the detected signal threshold; and
generating the downlink strength signal as a function of the time interval during which the single downlink control burst exceeds the detected signal threshold.

6. The method of claim 5, wherein the step of controlling the peak amplitude of the plurality of downlink data bursts includes adjusting the burst duration of the ramped envelope as a function of the down link strength signal to provide a threshold margin.

7. The method of claim 6, wherein the threshold margin is at least a 3 dB margin.

8. The method of claim 1, wherein the step of providing the one or more downlink control bursts includes providing a predetermined number of downlink control bursts, wherein each of the predetermined number of downlink control bursts is defined by a ramped envelope having a burst duration and a peak amplitude, and further wherein the burst duration and peak amplitude is different for each of the predetermined number of downlink control bursts.

9. The method of claim 8, wherein the step of providing a predetermined number of downlink control bursts includes providing each of the predetermined number of downlink control bursts in a predetermined time slot of a handshake between the implantable medical device and the external communication device.

10. The method of claim 8, wherein the step of detecting one or more of the downlink control bursts includes:
counting the number of downlink control bursts received by the receiver; and
generating the downlink strength signal as a function of the counted number of downlink control bursts.

11. The method of claim 10, wherein the step of controlling the peak amplitude of the plurality of downlink data bursts includes adjusting the burst duration of the ramped envelope as a function of the downlink strength signal to provide a threshold margin.

12. The method of claim 11, wherein the threshold margin is at least a 3 dB margin.

13. The method of claim 8, wherein the predetermined number of downlink control bursts is five downlink control bursts or less.

14. The method of claim 1, wherein the step of providing a plurality of downlink data bursts from the transmitter includes pulse interval modulating the plurality of downlink data bursts.

15. The method of claim 1, wherein the step of providing a plurality of downlink data bursts from the transmitter includes pulse width modulating the plurality of downlink data bursts.

16. The method of claim 1, wherein the step of controlling the peak amplitude of the plurality of downlink data bursts by adjusting the burst duration of the ramped envelope includes adjusting the burst duration in the range of about 5 $\mu$seconds to about 150 $\mu$seconds.

17. The method of claim 16, wherein the step of controlling the peak amplitude of the plurality of downlink data bursts by adjusting the burst duration of the ramped envelope includes adjusting the burst duration in the range of about 10 $\mu$seconds to about 50 $\mu$seconds.

18. The method of claim 1, wherein the implantable medical device is selected from the group consisting of:
a pacemaker, a defibrilllator, a pacemaker/cardioverter/defibrillator, a brian stimulator, a cardioveter/defibrillator, a neurostimulator, a muscle stimulator, a gastric stimulator, an implantable monitor, a hemodynamic monitor, and a drug pump.

19. A method for controlling downlink energy of telemetry signals transmitted from a transmitter of an external communication device to a receiver of an implantable medical device, the method comprising the steps of:
initiating a handshake by providing a handshake request from a transmitter of the implantable medical device;
receiving the handshake request at a receiver of the external communication device;
providing one or more downlink control bursts from the transmitter of the external communication device in response to the received handshake request, wherein each downlink control burst is defined by a ramped envelope having a burst duration and a peak amplitude;
detecting one or more of the downlink control bursts received at the receiver of the implantable medical device, and generating a downlink strength signal representative of the strength of the one or more downlink control signals
communicating the downlink strength signal to the external communication device;
providing a plurality of downlink data bursts from the transmitter of the external communication device after the handshake is completed, wherein the plurality of downlink data bursts are modulated with data, wherein each downlink data burst is defined by a ramped envelope having a burst duration and a peak amplitude, and further wherein the peak amplitude of the plurality of downlink data bursts being controllable by adjusting the burst duration of the ramped envelope as a function of the downlink strength signal.

20. The method of claim 19, wherein the step of communicating the downlink strength signal to the external communication device includes communicating the downlink strength signal in a handshake confirmation to the external communication device.

21. The method of claim 19, wherein the method further includes periodically reinitiating a handshake by providing a handshake request from a transmitter of the implantable medical device, receiving the handshake request at a receiver of the external communication device, providing one or more downlink control bursts from the transmitter of the external communication device in response to the received handshake request, detecting one or more of the downlink control bursts and generating a downlink strength signal representative of the strength of the one or more downlink control bursts received at the receiver of the implantable medical device, communicating the downlink strength signal to the transmitter of the external communication device, and providing a plurality of downlink data bursts from the transmitter of the external communication device after the reinitiated handshake is completed, wherein the peak amplitude of the plurality of downlink data bursts is controlled by adjusting the burst duration of the ramped envelope as a function of the downlink strength signal.

22. The method of claim 19, wherein the step of providing the one or more downlink control bursts includes providing a single downlink control burst, and further wherein the step of detecting one or more of the downlink control bursts includes:
  receiving the single downlink control burst at the receiver of the implantable medical device, wherein the receiver has a detected signal threshold;
  determining the time interval during which the single downlink control burst exceeds the detected signal threshold; and
  generating the downlink strength signal as a function of the time interval during which the single downlink control burst exceeds the detected signal threshold.

23. The method of claim 22, wherein the peak amplitude of the plurality of downlink data bursts being controllable by adjusting the burst duration of the ramped envelope as a function of the downlink strength signal to provide a threshold margin of at least about 3 dB.

24. The method of claim 19, wherein the step of providing the one or more downlink control bursts includes providing a predetermined number of downlink control bursts, wherein each of the predetermined number of downlink control bursts is defined by a ramped envelope having a burst duration and a peak amplitude, and further wherein the burst duration and peak amplitude is different for each of the predetermined number of downlink control bursts.

25. The method of claim 24, wherein the step of providing a predetermined number of downlink control bursts includes providing each of the predetermined number of downlink control bursts in a predetermined time slot of the handshake between the implantable medical device and the external communication device.

26. The method of claim 24, wherein the step of detecting one or more of the downlink control bursts includes;
  counting the number of downlink control bursts received by the receiver of the implantable medical device, and generating the downlink strength signal as a function of the counted number of downlink control bursts.

27. The method of claim 26, wherein the peak amplitude of the plurality of downlink data bursts being controllable by adjusting the burst duration of the ramped envelope as a function of the downlink strength signal to provide a threshold margin of at least a 3 dB margin.

28. The method of claim 24, wherein the predetermined number of downlink control bursts is five downlink control bursts or less.

29. The method of claim 19, wherein the peak amplitude of the plurality of downlink data bursts is controlled by adjusting the burst duration of the ramped envelope in a range of about 10 $\mu$seconds to about 50 $\mu$seconds.

30. The method of claim 19, wherein the implantable medical device is selected from the group consisting of:
  an implantable medical device selected from one of a pacemaker, a defibrillator, a pacemaker/cardioverter/defibrillator, a brain stimulator, a cardioverter/defibrillator, a neurostimulator, a muscle stimulator, a gastric stimulator, an implantable monitor, a hemodynamic monitor, and a drug pump.

31. A telemetry system, the system comprising:
  an external communication device, the external communication device including a downlink transmitter operable to transmit one or more downlink control bursts, wherein each downlink control burst is defined by a ramped envelope having a burst duration and a peak amplitude, wherein the downlink transmitter is further operable to transmit a plurality of downlink data bursts, wherein the plurality of downlink data bursts are modulated, by the transmitter, with data, and further wherein each downlink databurst is defined by a ramped envelope having a burst duration and a peak amplitude; and
  an implantable medical device, the implantable medical device including:
    a downlink receiver operable to receive one or more downlink control bursts from the downlink transmitter,
    detection circuitry associated with the downlink receiver to detect the strength of the one or more downlink control bursts transmitted by the downlink transmitter and generate a downlink strength signal representative of the detected strength, and
    an uplink transmitter operable to transmit the downlink strength signal to the external communication device; and wherein the external communication device further includes a controller to control the peak amplitude of the plurality of downlink data bursts by adjusting the burst duration of the ramped envelope thereof as a function of the downlink strength signal.

32. The system of claim 31, wherein the uplink transmitter of the implantable medical device is operable for transmitting a handshake request to the external communication device, and further wherein the downlink transmitter of the external communication device is operable to transmit the one or more control bursts to the implantable medical device in response to the handshake request.

33. The system of claim 32, wherein the uplink transmitter is operable to transmit the downlink strength signal in a handshake confirmation to the external communication device.

34. The system of claim 31, wherein the downlink transmitter is operable to transmit a single downlink control burst, and further wherein the detection circuitry includes timing circuitry to determine a time interval during which the single downlink control signal exceeds a detected signal threshold of the downlink receiver.

35. The system of claim 34, wherein the peak amplitude of the plurality of downlink data bursts transmitted by the downlink transmitter is controlled by adjusting the burst duration of the ramped envelope as a function of the downlink strength signal to provide a threshold margin.

36. The system of claim 35, wherein the threshold margin is at least a 3 dB margin.

37. The system of claim 31, wherein the downlink transmitter is operable to transmit a predetermined number of downlink control bursts, wherein each of the predetermined number of downlink control bursts is defined by a ramped envelope having a burst duration and a peak amplitude, and further wherein the burst duration and peak amplitude is different for each of the predetermined number of downlink control bursts.

38. The system of claim 37, wherein the downlink transmitter is operable to transmit each of the predetermined number of downlink control bursts in a predetermined time slot forming a handshake between the implantable medical device and the external communication device.

39. The system of claim 37, wherein the detection circuitry includes a counter for determining the number of downlink control bursts detected by the downlink receiver, the downlink strength signal generated as a function of the counted number of downlink control bursts.

40. The system of claim 39, wherein the peak amplitude of the plurality of downlink data bursts is controlled by adjusting the burst duration of the ramped envelope as a function of the downlink strength signal to provide a threshold margin.

41. The system of claim 40, wherein the threshold margin is at least a 3 dB margin.

42. The system of claim 37, wherein the predetermined number of downlink control bursts is five downlink control bursts or less.

43. The system of claim 31, wherein the external communication device further includes a modulator to pulse interval modulate the plurality of downlink data bursts.

44. The system of claim 31, wherein the external communication device further includes a modulator to pulse width modulate the plurality of downlink data bursts.

45. The system of claim 31, wherein the burst duration of the ramped envelope of the plurality of downlink data bursts is adjustable in the range of about 10 $\mu$seconds to about 50 $\mu$seconds.

46. The system of claim 31, wherein the implantable medical device is selected from a group consisting of a pacemaker, a defibrillator, a pacemaker/cardioverter/defibrillator, a brain stimulator, a cardioverter/defibrillator, a neurostimulator, a muscle stimulator, a gastric stimulator, an implantable monitor, a hemodynamic monitor, and a drug pump.

* * * * *